United States Patent
Lambourne et al.

(10) Patent No.: US 10,378,319 B2
(45) Date of Patent: Aug. 13, 2019

(54) PROCESS OF SUSTAINING METHANE PRODUCTION IN A SUBTERRANEAN CARBONACEOUS MEDIUM

(71) Applicant: Commonwealth Scientific and Industrial Research Organisation, Parkville (AU)

(72) Inventors: David Lambourne, Carlton North (AU); Philip Hendry, Leichhardt (AU)

(73) Assignee: COMMONWEALTH SCIENTIFIC AND INDUSTRIAL RESEARCH ORGANISATION, Campbell, Australian Capital Territory (AU)

( * ) Notice: Subject to any disclaimer, the term of this patent is extended or adjusted under 35 U.S.C. 154(b) by 551 days.

(21) Appl. No.: 15/106,214

(22) PCT Filed: Dec. 19, 2014

(86) PCT No.: PCT/AU2014/001150
§ 371 (c)(1),
(2) Date: Jun. 17, 2016

(87) PCT Pub. No.: WO2015/089566
PCT Pub. Date: Jun. 25, 2015

(65) Prior Publication Data
US 2016/0319643 A1 Nov. 3, 2016

(30) Foreign Application Priority Data

Dec. 19, 2013 (AU) .................................. 2013904965
Dec. 19, 2013 (WO) ................ PCT/AU2013/001488

(51) Int. Cl.
*E21B 43/00* (2006.01)
*C09K 8/582* (2006.01)
(Continued)

(52) U.S. Cl.
CPC ............ *E21B 43/006* (2013.01); *C09K 8/582* (2013.01); *C12P 5/023* (2013.01); *E21B 43/16* (2013.01);
(Continued)

(58) Field of Classification Search
CPC ........ E21B 43/006; E21B 43/16; C09K 8/582
(Continued)

(56) References Cited

U.S. PATENT DOCUMENTS

| | | | |
|---|---|---|---|
| 2004/0033557 A1* | 2/2004 | Scott ...................... | C09K 8/582 435/42 |
| 2011/0250582 A1* | 10/2011 | Gates ..................... | C09K 8/582 435/3 |

FOREIGN PATENT DOCUMENTS

WO 2011080518 7/2011

OTHER PUBLICATIONS

International Search Report dated Jan. 19, 2015 corresponding to International Patent Application No. PCT/AU2014/001150; 2 pages.

* cited by examiner

*Primary Examiner* — Zakiya W Bates
*Assistant Examiner* — Ashish K Varma
(74) *Attorney, Agent, or Firm* — Leason Ellis LLP

(57) ABSTRACT

Process for stimulating and maintaining the activity of a microbial consortia within a subterranean solid carbonaceous medium to produce methane are described. The process comprises the steps of: (A) dosing a first nutrient composition into the microbial consortia environment, (B) monitoring the microbial consortia environment, including the generation of methane therein; (C) dosing a second nutrient composition into the microbial consortia based upon the results of step (B); and (D) repeating steps (B) and (C) and, if required, (E) dosing a further nutrient composition
(Continued)

into the microbial consortia environment based upon the results of step (D).

22 Claims, 5 Drawing Sheets

(51) Int. Cl.
*E21B 43/16* (2006.01)
*C12P 5/02* (2006.01)
*E21B 47/00* (2012.01)
*E21B 49/00* (2006.01)
*E21B 49/08* (2006.01)
*G01N 33/00* (2006.01)

(52) U.S. Cl.
CPC .............. *E21B 47/00* (2013.01); *E21B 49/00* (2013.01); *E21B 49/08* (2013.01); *G01N 33/0047* (2013.01); *Y02E 50/343* (2013.01)

(58) Field of Classification Search
USPC ........................................................ 166/246
See application file for complete search history.

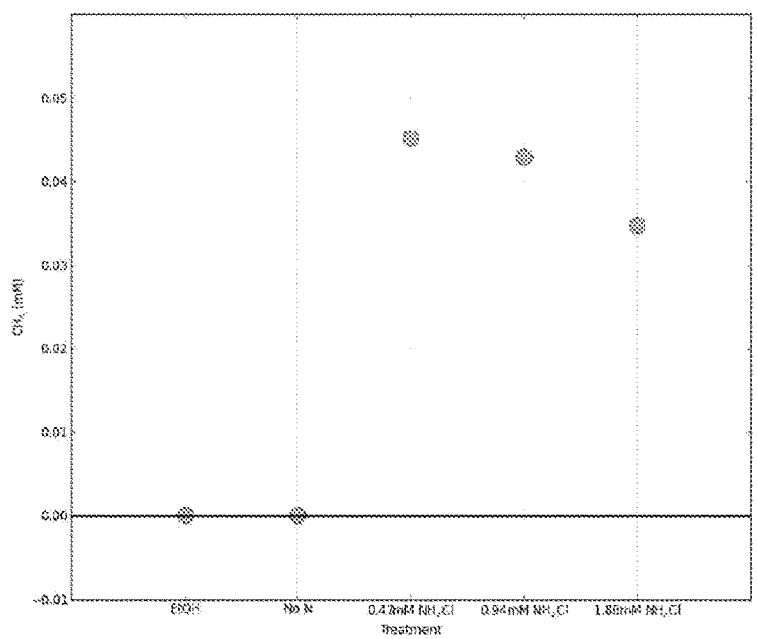
Figure 5
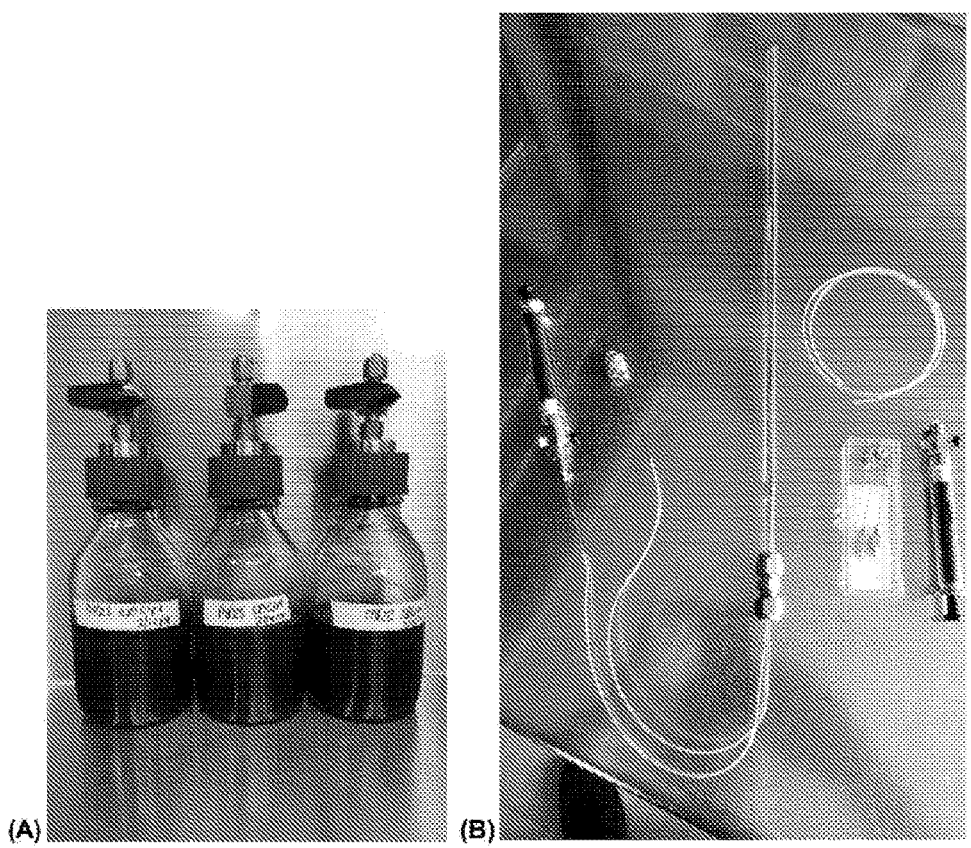
Figure 6(a) and (b)

PROCESS OF SUSTAINING METHANE PRODUCTION IN A SUBTERRANEAN CARBONACEOUS MEDIUM

FIELD

The present invention relates to the microbial production of methane from subterranean carbonaceous media and more particularly to the dosing of nutrients to enhance production thereof.

BACKGROUND

Methane is associated in varying amounts with most coal deposits. It may be formed thermogenically during burial and thermal maturation of the coal or it may be produced biogenically by the action of microbes. Bacteria are considered to be the primary degraders of compounds in coal, producing a range of intermediates which are successively degraded to methane precursors, such as hydrogen gas, carbon dioxide, acetate and various other compounds (e.g. dimethyl sulfide, formate, methanol and methylamines). These precursors are then converted to methane via methanogenic archaea. This methanogenic process may occur via a number of mechanisms including $CO_2$ reduction, acetoclastic (from acetate) processes and methylotrophic processes.

The coal seam environment in which biogenic methane is produced is anoxic and reducing. Due to macronutrient limitation biogenic methane production is slow and occurs over long time-scales.

Production from a typical coal seam methane (CSM) well may occur for 5-7 years, after which time, the rate of production generally becomes uneconomic and the well may be abandoned.

It may be possible to prolong the production life of the well by introducing methanogenic microbial populations. For example, U.S. Publication No. 2004/0033557 describes introducing a consortium of selected anaerobic microorganisms into a subsurface formation for in situ conversion of organic compounds into methane and other compounds.

Furthermore, it may also be possible to relatively rapidly replenish the methane within a buried coal seam by stimulation/invigoration of the microbes that reside in the coal and/or associated water. It is known that this can be achieved by addition of nutrients to the system. For example, U.S. Pat. No. 7,832,475, the relevant contents of which are incorporated herein by reference, describes a method for enhancement of biogenic methane production that involves introducing an indiscriminate microbial population stimulant, such as corn syrup, emulsified oil, and/or milk, to blanket boost microbial populations in a hydrocarbon-bearing formation. The method further involves subsequent manipulation of the microbial populations by selectively starving one or more microbial populations to selectively sustain at least one of the boosted microbial populations.

In particular, U.S. Pat. No. 6,543,535, the relevant contents of which are incorporated herein by reference, provides a process to enhance methane recovery through a process of methodically analysing the microbial consortia and its subterranean environment to determine what changes are required in the ecological environment to promote microbial generation of methane. While the underlying principles have been beneficial in enhancing methane recovery in a significant number of hydrocarbon bearing subterranean formations, sustained in situ microbial activity is not always achieved.

Furthermore, U.S. Pat. No. 6,543,535 discloses a process for stimulating the activity of microbial consortia in a hydrocarbon-bearing, subterranean formation to convert hydrocarbons present to methane gas. In summary, the process includes the steps of: (i) analysing the formation; (ii) detecting and characterising the microbial consortia; (iii) utilising the previously acquired information to determine ecological conditions that promote in-situ microbial methane production; and modifying the formation environment accordingly to stimulate microbial conversion of hydrocarbons to methane. Furthermore, this document teaches that the addition of suitable substances to promote the growth of the microorganism include nitrogen and phosphorus. However, U.S. Pat. No. 6,543,535 is primarily directed to optimal methane production from a liquid carbonaceous medium, in particular from oil reservoirs. In contrast to liquid carbonaceous medium, solid carbonaceous medium, such as coal, is more heterogeneous and the reaction kinetics often substantially slower. As a result, the teachings of U.S. Pat. No. 6,543,535 cannot be directly transferred to a solid carbonaceous medium in order to achieve sustainable methane production.

Any discussion of the prior art throughout the specification should in no way be considered as an admission that such prior art is widely known or forms part of common general knowledge in the field.

It is an object of the present invention to overcome or ameliorate at least one of the disadvantages of the prior art, or to provide a useful alternative.

An object of a preferred embodiment of the invention is provide a process of further accelerating and sustaining biochemical conversion of solid hydrocarbons to methane at a rate that is commercially practical or establishing and/or maintaining an in situ environment that supports commercial rates of hydrocarbon conversion and methanogenesis.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

SUMMARY OF THE INVENTION

According to a first aspect of the present invention there is provided a process of stimulating and maintaining the activity of a microbial consortia within a subterranean solid carbonaceous medium to produce methane comprising the steps of:
  A. dosing a first nutrient composition into a microbial consortia environment;
  B. monitoring the microbial consortia environment, including the generation of methane therein;
  C. dosing a second nutrient composition into the microbial consortia environment based upon the results of step (B); and
  D. repeating steps (B) and (C) and, if required,
  E. dosing a further nutrient composition into the microbial consortia environment based upon the results of step (D).

In one embodiment, there is provided a process of stimulating and maintaining the activity of a microbial consortia within a subterranean solid carbonaceous medium to produce methane comprising the steps of:
  A. dosing a first nutrient composition into a microbial consortia environment;
  B. monitoring the microbial consortia environment, including the generation of methane therein;

C. dosing a second nutrient composition into the microbial consortia environment based upon the results of step (B).

In another embodiment, the invention provides a process of stimulating and/or maintaining the activity of a microbial consortia within an endogenous or exogenous subterranean carbonaceous medium, that can be produce methane comprising the steps of:
  A. dosing a first nutrient composition into the microbial consortia environment of the medium;
  B. monitoring the microbial consortia environment of the medium;
  C. dosing a second nutrient composition into the microbial consortia based upon the results of step (B); and
  D. repeating steps (B) and (C) and, if required,
  E. dosing a further nutrient composition into the microbial consortia environment based upon the results of step (D).

It will be understood that monitoring the microbial consortia environment of the medium can include the monitoring of the generation of methane therein.

It will also be understood that the subterranean carbonaceous medium can be endogenous material or an exogenous material that is taken from its place of origin, to a laboratory for testing, and characterisation, etc.

It will be appreciated that the term 'further nutrient composition' is used interchangeable herein with 'subsequent nutrient composition', and the first dosing in A is also described as the 'first' or 'initial' dose or dosing. Furthermore, the term 'microbial consortia within an endogenous or exogenous subterranean carbonaceous medium' is used interchangeably with the term 'system' when the context makes it is clear that it is acceptable to reference these features in such a manner. Finally, the period/interval B above is also known herein as an 'incubation' period.

The generated methane is preferably recovered after the completion of the dosing of each of the nutrient compositions, although methane collection and the dosing of the nutrient composition may also occur concurrently.

In a preferred embodiment, each of the nutrient composition doses or dosages is delivered to produce an amended indigenous environment (i.e. nutrient composition plus indigenous environment of the microbial consortia) which is allowed to incubate, thereby stimulating the microbial consortia to grow, and/or produce methane. The stimulation may also be to an existing methane generating consortia, whereby the stimulation encourages the consortia to grow better and to generate higher levels of methane in gases produced.

The nutrient composition of the invention preferably comprises at least nitrogen and/or phosphorus.

Preferably, the second composition and/or subsequent nutrient composition has a lower nitrogen concentration than the first nutrient composition. Suitably, the second composition and/or subsequent nutrient composition may have up to a 90% or more reduction in nutrient level. For example, the nitrogen reduction in successive cycles may be from 10-100% of a reduction from the previous cycle. More specifically, the reduction may be 10%, 20%, 30%, 40%, 50%, 60%, 70%, 80%, 90%, or even 100%, particularly for the nitrogen component. In certain embodiments, the reduction is a 25%, 50%, or 75% reduction in nitrogen, and all intermediate values, if deemed appropriate from investigative studies.

The duration of monitoring/incubation period (B), starting after the completion of the first dosing of the nutrient composition, will depend upon the microbial consortia, its amended environment and the desired commercial methane production rate. However, it would be typically expected that the incubation period would be between seven days and three years, more preferably between two months and two years and even more preferably between six months and 18 months. In the case of the shorter time frames, less than 2 months, for example, it will be understood that these period are particular to the methods of the invention when applied to laboratory or small scale stimulations/models, rather than field studies where the longer intervals of >2 months/years are more appropriate.

Preferably, the monitoring of the microbial consortia environment is undertaken during the dosing phase; the incubation phase and/or the methane recovery phase. More preferably, monitoring is conducted over all of the stages of the process. It should be noted that the more extensive the monitoring of the microbial consortia environment that occurs, the better the knowledge of how the microbial consortia is expected to respond to nutritional and/or environment stimuli. This enables tailored second and/or subsequent nutrient compositions for better control and more sustainable production of biogenic methane on a commercial basis.

In certain embodiments, for example, where sampling for monitoring methane generation occurs periodically, the incubation period could be weekly, fortnightly, or even annually. Indeed, and preferably in same embodiments, for sample where the environment is particularly dynamic or reactive, sampling/monitoring could be substantially continuous where intervals between consecutive samples are very short, for example, second, minutes, hours or even daily.

Again, in the case of the shorter sampling/analysis time frames it will be understood that these period are particular to the methods of the invention when applied to laboratory or small scale stimulations/models, rather than field studies where the longer intervals of >2 months/years are more appropriate, although with substantially continuous monitoring sensors, a essentially continuous monitoring can be undertaken, even in the field.

The recovery of methane preferably occurs as part of a cyclic process comprising a dosing phase (i.e. dosing of the nutrient composition), an incubation phase and a methane recovery phase. Suitably, the recovery of methane may occur over at least two process cycles, preferably over at least three cycles or more preferably still, until the catchment area is no longer commercially sustainable.

In one embodiment, the timing for dosing of the second and subsequent nutrient compositions may be determined after observation of a parameter associated with a peak of methane generation for a given cycle/incubation period for a particular dosing cycle. It should be understood that the parameter associated with a peak of methane generation will be the highest of a number of data point parameters sampled while monitoring an incubation period.

Suitably, the parameter associated with methane generation can be any parameter that is related to, and/or, associated with changes in level of methane generation, that is, increasing and decreasing methane levels.

Desirably, the parameter associated with monitoring methane generation is one or more of:
  (i) methane generation, preferable measured as % methane/volume, moles or mole % of methane/volume;
  (ii) average daily rate of methane generation over a monitoring/incubation period (B);
  (ii) average daily % contribution to a sample methane composition over a monitoring/incubation period (B);

(iii) average amount of methane generated over a monitoring/incubation period (B); and
(iv) gas pressure/partial pressure, thermal or ionic conductivity or isotopic ratio measurements associated with methane gas composition concentration.

Preferably, the parameter is one which can highlight a maximum/peak amount or quantity of methane generated and/or a peak rate of methane generation, after which a preferably steady reduction in the amount or quantity and/or rate of methane generation can be observed.

It will be understood that where a number of parameters have been determined and a change in the parameter can indicate that methane generation trend is increasing or decreasing at any point in time or over any given interval of time, for a particular incubation period/cycle. Where consideration of the parameters reflects an increase in methane production, it will be understood that no remedial action will be required at that particular time.

Similarly, when the change in parameter indicates that methane generation has surpassed a maximum level, it will be understood that this is indicative that the methane generation performance of the system is becoming less efficient. Therefore, when a suitably low point is reached, this signals that remedial action should be taken to improved the performance/efficiency. Thus, the second or subsequent nutrient dose of the invention can be provided to the system.

In a preferred embodiment, the peak methane generation parameter monitored over a given monitoring/incubation period (B) is one or more of:
(i) a peak rate of methane production per unit nitrogen $(M_r/N)^n$ resulting from a nitrogen concentration added in the second $(N_c)^2$ or subsequent $(N_c)^n$ nutrient composition dosages is higher than a peak rate of methane production per unit nitrogen $(M_r/N)^1$ observed for the initial nutritional composition dosage $(N_c)^1$, wherein n is dose 2, 3, 4, 5, 6, 7, 8, 9, 10, ... n+1;
(ii) a peak rate of methane production per unit nitrogen $(M_r/N)^n$ resulting from the nitrogen concentration added in a second $(N_c)^2$ or subsequent $(N_c)^n$ nutrient composition dosages is greater than a peak rate of methane production per unit nitrogen $(M_r/N)$ observed for an initial nutritional composition dosage, than had the second or subsequent dosages the same or higher nitrogen concentration $(N_c)^n$ than the initial nitrogen dosage concentration $(N_c)^1$, wherein n is dose 2, 3, 4, 5, 6, 7, 8, 9 or 10, ... n+1;
(iii) a peak average daily % contribution to a sample methane composition over a sampling period $(avc)^1 > (avc)^n$, wherein n is dose 2, 3, 4, 5, 6, 7, 8, 9, n+1; or
(iv) peak mole of methane generated per volume of methane gas, where (moles/unit volume methane gas)>(moles/unit volume methane gas)$^n$, wherein n is dose 2, 3, 4, 5, 6, 7, 8, 9, 10, ... n+1; and
(v) average amount of methane generated during the period.

Typically, the number of cycles 'n' required will be dictated by when the system cannot be further stimulated into generating methane.

Once selected, if required, the parameter and/or peak parameter can be normalised for a given nutrient concentration in a particular cycle and/or for a given volume of gas generated. In some embodiments, these parameters can be averaged over an entire incubation period, other otherwise manipulated, so that a convenient comparison can be made to the parameter when normalised to a different nutrient concentration in a different cycle.

Suitably, the parameter associated with the maximum amount or quantity of methane generation produced and/or a peak rate of methane generation preferably is measured at least once per incubation/dosing cycle, or a series of parameters can be averaged to indicate a general trend associated with a cycle/incubation period. If the parameter is below a predetermined level, this indicates that remedial action is required. If singe parameter is not below a predetermined level, this indicates that no remedial action is required. The predetermined values can be selected based on previous studies around the formation and consortia environment, or can be based on a % change in the corresponding parameter for the previous cycle.

While a single sample point is be utilised in this manner, it is preferable that two or more, and indeed a plurality of sample points, such as substantially continuous sampling monitoring, is carried out during each incubation period/dosing cycle. This is because the more methane generation data available for a particular incubation allows subtle and/or dramatic increases/decreases in methane generation to be observed. In this manner, peak parameters can be easily and accurately identified and remedial actions can be initiated swiftly.

Thus in one embodiment, for example, where a substantially continuous gas sensor rapidly measures evolved gas composition, the parameter may be as simple as methane concentration, measured for example, with respect to: % composition (relative to a know volume of gas), mg/dm$^3$, molarity (m/dm$^3$), etc. Similarly, the parameter might be an isotopic ratio, a thermal or ionic conductivity measurement or a gas or partial pressure value that is associated with discrete changes in the evolved gas composition.

In another embodiment, the parameter may correspond to the rate of methane generation over any given time/sampling interval. In this case, observation of a reduction in a maximum/peak rate of methane generation will signal that the system is likely to benefit from commencement of a second dosing cycle according to the invention.

In one embodiment, the maximum/peak rate of methane generation may be determined starting by calculating the average daily rate of methane generation over a given incubation period. It will be understood that the average daily rate of methane generation can be determined by considering the volume of methane gas recovered from a gas samples collected over a set time/incubation period.

Thus, changes in the rate of methane generation per unit volume of evolved gas generated for a given nutrient concentration for any incubation period can be calculated. This information can be used to make a determination as to the effect of variation nutrient dosages into a particular consortia environment over a given interval. Thus, the average daily rate of methane generation prior to initial dosing can be used as a baseline, and compared with a peak rate of methane generation per unit of nitrogen for first/initial, second and/or subsequent nutrient doses where required. This facilitates the initiation of remedial action, where necessary in accordance with the present invention, such that flagging methane production can be reinvigorated and/or optimised and/or prolonged compared to where no nutrient dosing regimen is followed. The method of the invention thereby improves the efficiency and sustainability of coal seam methane recovery.

In another embodiment still, the parameter may correspond to an average daily % contribution to a sample methane composition that is collected over a given sampling period. For example, for a system generating methane and tending towards increased efficiency, in a sampling/sample collecting interval of 10 days, a methane gas composition of 5% can be determined (by GC for example). In this case, the average daily % contribution to the methane composition would be 0.2%. If this level of methane production is for an incubation cycle involving 100 mg/L nitrogen component, then the average daily % contribution to the methane composition per unit nitrogen parameter would be 0.002. Thus, for an increasingly efficient system, this parameter will increase, whereas after maximum efficiency has been surpassed, this parameter will start to decrease, thereby indicating that the system is beginning to become less efficient, signalling remedial action is suitable/desirable.

Furthermore, in some embodiments, for second and/or subsequent doses, particular where sampling intervals are used to gather a volume of gas for analysis, the volume of gas produced may be smaller than the initial or previous cycle/incubation period. However, preferably, the concentration of methane present in the smaller volume is higher than that observed for previous cycles. Where the methane concentration per unit volume is higher, this may be indicative that, while overall, the consortia are producing less gas, the microbes that are active are more efficiently converting feedstock and/or nutrients into methane than was the case for the previous cycle.

It will be understood that in some embodiments, for second and/or subsequent doses, the volumes of evolved gases may be the same or even greater that the initial or previous doses. In such case, it is expected that the methane concentration will also be higher.

Advantageously, considering increases and decreases in evolved gases and methane compositional changes will allow the skilled person to better under the methane generation processes in the formation to better allow approximations to be made as to the sustainability/potential lifetime of a particular system.

The process of the invention is particularly advantageous when the carbonaceous medium is solid, such as in the case of coal and carbonaceous shale. These media often comprise localised indigenous environments relating to variation in organic matter (maceral) composition (i.e. differences in relative amounts of liptinite, vitrinite and inertinite). Thus, methane production can greatly vary within the formation and certain areas will comprise more appropriate feedstock and feedstock access for certain consortia than others. The problem can be compounded over time as environment conditions in these areas are dynamic over time so that a single type and/or dose of nutrients etc will not always be suitable for repeat use in the same area.

The inherent unpredictability of methanogenesis from heterogeneous solid carbonaceous medium is in contrast to the more homogeneous liquid based carbonaceous media, such as the relatively homogeneous system described in U.S. Pat. No. 6,543,535 where the medium/feedstock is essentially liquid whereby microbes can more easily surround/become dispersed in the feedstock so that they have better access than to an oil feedstock for example. The localised indigenous environments found in coal seams are heterogeneous and localised variations can make sustainable methane production difficult, especially on a commercial basis, since variations in the natural environment means that certain areas are more suitable for methane product that others, leading to risk of inconsistencies in methane generation in these areas. For example, in some carbonaceous media, microbial enhanced methane production, whilst initially successful, often falters after a short period of time, with the existing microbial consortia dropping to unviable levels that are unsuitable to maintain commercial production. This may result from the differences in nature between oil/hydrocarbon fields and carbonaceous medium formations. In the latter case, since the carbonaceous medium is the microbial feedstock, that is a solid material such as the coal or shale, the ease of access of microbial consortia to the feedstock is much more curtailed compared to the more homogeneous feedstock conditions experienced for liquid/gaseous feedstocks. Therefore, the present invention provides an alternative, improved system for allowing sustained and/or prolonged methane recovery from solid carbonaceous medium formations, such a coal and/or shale seams/formations whereby existing methods for these systems are not as transferable to coal or other solid feedstock systems.

As explained herein, the process of the present invention uses periodic monitoring of the indigenous environment to periodically modify the external nutrient composition dosage to compensate for temporal variations in the indigenous environment, including changes in formation water and/or microbial consortia, as well as spatial variations in organic matter composition and/or essential nutrient levels. As the microbial consortia consume carbonaceous media over time, the temporal variations in the indigenous environment may be related to spatial variations in the indigenous environment.

As explained above, the elapsed time between the end of dosing of the first nutrient composition (step A) and the start of dosing the second nutrient composition (Step C), for example, the first incubation period, will depend on when the performance/efficiency of a particular system is observed to be in decline. The period/time will also depend on whether the system in question is a laboratory simulation/model or otherwise, such as a coal field.

In any case, the elapsed time between the end of dosing of the first nutrient composition (step A) and the start of dosing the second nutrient composition (Step C), can range anywhere from between 7 days and 36 months, more preferably between 1 month and 24 months, and even more preferably, is between 4 months and 18 months. These periods are also applicable to the second and/or subsequent dosing cycle(s). However, in some cases, particularly for simulation testing/sample monitoring purposes, the interval may range anywhere from 1 to 52 weeks, more preferably 2 to 36 weeks. In certain simulations the period/interval is preferably 1 to 4 weeks, including, for example, 14 and 21 day intervals.

In some instances, depending on the circumstances, these time frames are also applicable to sampling periods within a particular incubation period and it will be understood that as many sampling points necessary within any given incubation period can be utilised to determine when further dosing/environmental adjustment action is required.

Although, as explained above, in some preferred embodiments, the sample interval can be very small/short, such that sampling is preferably effectively substantially continuous to the limit of any analytical instrumentation used in the sampling/analysis determination.

In any case, the period of time for incubation and/or monitoring/sampling will be dependent upon the initial indigenous environment including the state of any indigenous microbial consortia suitable for methane formation. As such, the elapsed times will be dictated by the results of the monitoring/sampling, and in particular, observation of a decrease in the amount/rate methane being produced over a given time interval for any particular system.

In an alternative embodiment, rather than ending with the dosing of the first composition, the rate of dosing of the initial composition may be significantly reduced, preferably in stepped changes, wherein the combined indigenous and/ or external components are monitored to assess a reduced dosage level which is required to maintain a sustainable level of methane production. The reduction in dosage rate, which could be a reduction of up to 90% or more of the initial rate, will be determined by the level required to sustain maximum rates of methane production. In certain embodiments, the reduction could be from 5% to 99%, or any amount between depending on the circumstances. As distinct from adjustment in the dosage level of the external nutrient composition to bring the methane production levels to within expectations during the initial commission phase, in this embodiment, the second nutrient composition will be delivered specifically in timing, magnitude and/or composition to address specific changes in the indigenous environment.

As described herein, it will be understood that a peak/maximum of methane generation can be identified by measuring/monitoring a parameter associated with the amount and/or rate of methane generation that occurs periodically over a certain time frame, so that a peak methane generation amount/rate can be observed prior to a preferably steady and consistent reduction in the methane production thereafter. For second and subsequent cycles, one parameter of interest is the peak methane generation rate per unit nitrogen provided per dosing cycle. In other embodiments, the parameter can be peak methane concentration, a peak thermal or ionic conductivity measurement, a peak gas pressure or partial pressure, as well as a peak/maximum average daily % contribution to a methane composition that is collected over a given number of sampling periods of varying intervals.

Thus, step (B) measures, and/or identifies a peak methane generation parameter, such as concentration and/or rate, and the second nutrient composition is dosed after the methane generation has dropped to less than 95%, 90%, 85%, 80%, 75%, 70%, 65%, 60%, 55%, or 50% of the peak methane generation parameter.

More preferably, the second nutrient composition is dosed after the methane generation has dropped to less than 50% of the peak methane generation parameter, for example, amount/rate. The greater the reduction in methane production observed, the firmer the indication that the indigenous environment has significantly changed to the detriment of methane production. It has been observed that certain methanogenic stock cultures that have ceased methane production, can be stimulated/re-invigorated by addition of a 100/400 ratio N/P (nitrogen/phosphorous) nutrient component to result in gas and methane productivity returning to normal levels. However, to avoid an overly slow recovery in the methane production, the second nutrient composition should ideally be dosed after the methane generation has dropped to no lower than 1%, more preferably, no lower than 10% and even more preferably, no more than 20% of a peak methane generation parameter, such as rate.

The initiation of the second cycle of the dosage regimen of the invention within this range enables microbial consortia activity to recover with the appropriate stimuli in the form of the second (or further) nutrient dosage regimen.

Preferably guided by a model of the in-situ stimulation of methanogenesis (including a model of the indigenous environment) but not limited to same, the second nutrient composition is dosed into the indigenous environment, wherein said second nutrient composition is different to the first nutrient composition as described herein.

In one embodiment, the difference between the first nutrient composition and the second and/or subsequent nutrient composition is a decrease in the proportion of nitrogen relative to the total amount of nitrogen and phosphorus in the nutrient compositions.

In the context of the methods of the present invention, the peak methane production, calculated in one embodiment as an average rate of methane generated over period of time before any extraneous nutrients are provided, provides a baseline level for assessment of a suitable dosing regimen to be added to the system when methane production drops below a particular undesirable level. As explained elsewhere herein, the dosing of the first/initial nutrient composition results in stimulation of the system such that an initial parameter of methane production per unit nutrient dosage arises $(M_r)^1$. Comparison of this parameter for the initial and second, or second and subsequent dosing steps, indicates whether or not the dosing regimens provide a beneficial effect for second and subsequent cycles where nitrogen levels/concentrations are sequentially reduced.

Thus, when the peak parameter of methane production per unit nitrogen is surpassed for a particular dosing cycle, the next reduced nutrient dosage can be delivered to the microbial consortia environment to effect a reinvigoration of methane production.

In accordance with the invention, as explained above, the dosage of certain nutrients, for example, nitrogen, in these later doses can be reduced with respect to the initial or preceding dose.

Thus, in one embodiment, the second and/or subsequent dose gives rise to an increase in the rate of methane production per unit nitrogen nutritional component ('N'—unit nitrogen nutrient component concentration) compared to the peak rate of methane production observed for the cycle immediately preceding the second or subsequent dose respectively.

In a preferred embodiment, the method of the invention is such that the peak parameter of methane production per unit nitrogen component $(M_r/N_c)^n$ resulting from the nitrogen concentration added in the second $(N_c)^2$ or subsequent $(N_c)^n$ nutrient composition dosages is higher than peak parameter of methane production per unit nitrogen component $(M_r/N_c)^1$ observed for the initial nutritional composition dosage $(N_c)^1$, wherein n is dose 2, 3, 4, 5, 6, etc, . . . n+1.

In this embodiment, $(M_r/N_c)^n > (M_r/N_c)^1$, wherein $(N_c)^n < (N_c)^1$.

In a preferred embodiment, the method of the invention is such that the peak rate and/or concentration of methane production per unit nitrogen component $(M_r/N_c)^n$ resulting from the nitrogen component concentration added in the second $(N_c)^2$ or subsequent $(N_c)^n$ nutrient composition dosages is higher than peak rate and/or concentration of methane production per unit nitrogen component $(M_r/N_c)^1$ observed for the initial nutritional composition dosage $(N_c)^1$, wherein n is dose 2, 3, 4, 5, 6, etc, . . . n+1.

In this embodiment, $(M_r/N_c)^n > (M_r/N_c)^1$, wherein $(N_c)^n < (N_c)^1$.

For example, an initial 100 mg/L dose of the nitrogen nutritional component (N), providing a rate of methane production per unit nitrogen component of "x", will be less than the rate of methane production per unit nitrogen nutritional component "y" arising from a second dose, when the second dose is <100 mg/L of the nitrogen nutritional component.

In another embodiment, the second and/or subsequent nitrogen dose may give rise to a greater increase in the rate and/or concentration of methane production per unit nitrogen component, than if the second and/or subsequent nitrogen component dose had the same or higher nitrogen component dose than the initial dosage.

More specifically, for example, an initial dose of 100 mg/L for the nitrogen (N) nutritional component giving a rate of methane production per unit nitrogen component of 0.0008, will be less than the rate of methane production per unit nitrogen component of 0.00108 resulting after a dose of 75 mg/L of nitrogen nutritional component (N) is introduced into the system in a second cycle.

In yet another embodiment, the second and/or subsequent nutrient composition(s) comprises substantially no nitrogen component. For the purposes of the present invention, substantially no nitrogen component in the nutrient compositions means nitrogen nutrient component (N) levels which are no more than trace amounts, corresponding to impurities levels of other constituents making up the nutrient composition.

Thus, in a preferred embodiment, the method of the invention is such that the peak rate of methane production per unit nitrogen component $(M_r/N_c)^n$ resulting from the nitrogen concentration added in a second $(N_c)^2$ or subsequent $(N_c)^n$ nutrient composition dosages is greater than the peak rate of methane production per unit nitrogen component $(M_r/N_c)$ observed for an initial nutritional composition dosage, than had the second or subsequent dosages the same or higher nitrogen component concentration $(N_c)^n$ than the initial nitrogen component dosage concentration $(N_c)^1$, wherein n is dose 2, 3, 4, 5, 6, etc, . . . n+1.

In this embodiment, $(M_r/N_c)^n > (M_r/N_c)^1$ where the nitrogen nutrient component concentration $(N_c)^n \geq (N_c)^1$.

For example, if an initial 100 mg/L dose of nitrogen nutrient component (N) provided a rate of methane production per unit nitrogen component of "x", this rate "x" would be greater than the rate of methane production per unit nitrogen component arising from a second dose that had a 100 mg/L dose of nitrogen nutrient component (N) or more.

More specifically, an initial N dose of 100 mg/L giving a rate of methane production per unit nitrogen of 0.0008, will be higher than the rate of methane production per unit nitrogen component concentration of 0 (zero) observed when a second dose of N dose of 100 mg/L is introduced to the system 14 days later.

The above desirable effects arising from the methods of the invention unexpectedly relate to more efficient methane production per unit nitrogen N dose resulting from dosing less nitrogen nutrient into the system over time, that is, a reduction in the nitrogen dose going from initial to second and/or subsequent nutrient composition dosages.

In short, methane production from the microbial consortia environment is surprisingly enhanced through dosage of second and/or subsequent nutrient composition comprising less nitrogen that the initial/previous nutrient dosage.

This is an unexpected result, whereby methane production is surprisingly enhanced through the dosage of a nutrient composition comprising less nitrogen N in later doses compared to the initial or previous nutrient concentration used to stimulate methanogenesis by a particular consortia.

The inventors have demonstrated that a simulated methanogenesis model, when dosed with a nutrient composition with reduced a nitrogen component dosage, performs better than when the simulation/model is dosed with a repeated or greater nitrogen component N level in the second dosage. Thus, methane production is surprisingly enhanced through a dosage regimen involving periodic dosing of a nutrient composition comprising less N than the initial or previous nutrient composition used to stimulate methanogenesis by a particular consortium in a particular indigenous environment.

Suitably, the second and/or subsequent nutrient dosing composition have a phosphorus nutrient concentration that is the same or different to the initial or previous dosing step(s).

In another embodiment, another difference between the first nutrient composition and the second or subsequent nutrient composition is a decrease in the proportion of phosphorus relative to the total amount of nitrogen and phosphorus in the nutrient compositions.

While not wanting to be bound by theory, it is thought that reduced levels of nitrogen are required compared to the first nutrient composition due to the activity of the initial microbial consortia being not sufficient to efficiently extract indigenous sources of nitrogen and/or the organic components (e.g. maceral entities) changing over time, such that more indigenous nitrogen becomes available, such that less supportive extraneous nitrogen is required. In an extreme case, no further extraneous nitrogen is required, as sufficient support has already been provided to the bacteria, such that they are capable of breaking indigenous nutrient precursors. In this instance, too much extraneous nitrogen can have a undesirable effect on the system.

Just as the indigenous environment will have different levels of available nitrogen over time, the indigenous environment will have different levels of all nutrient requirements over time, for example, phosphorus, vitamins, trace elements, etc., and combinations thereof. Through the monitoring of the indigenous environment over time, in addition to the nitrogen component, one or more additional components of the second or further nutrient composition may be adjusted to ensure that the microbial consortia is not adversely affected by a deprivation of one or more nutrients.

In addition to the process of the present invention ensuring sustainable methane production through providing additional supplemental doses of nutrients, the process may also be used to avoid the excessive dosage of one or more nutrient components, including nitrogen. This is desirable from the environmental perspective.

Preferably, the difference between the first nutrient composition and second or subsequent nutrient composition, for example, in certain nutrient levels, is determined by reference to one or more differences in:
  formation water;
  the carbonaceous medium, and/or
  the microbial consortia,
  between the dosing of the first nutrient composition and second and/or subsequent nutrient composition (or the analysis of the indigenous environment prior to, and leading to, the dosing of the second or subsequent nutrient composition). Analysis of the indigenous environment may involve monitoring changes in one or more of pH, ionic strength, etc.

Preferably, the requirements of the first, second and/or subsequent nutrient composition(s) is determined through the use of an algorithm. The algorithm is preferably an adaptive learning algorithm (i.e. an algorithm which uses data from previous monitoring cycle(s) of the indigenous environment to control the current dosage regimen). The accumulation of historical input (initial indigenous environment, discrete changes to same over time particularly with respect to dosage of known external nutrient compositions) and output (e.g. actual observed methane production and changes in same which result from induced and natural changes in the indigenous environment) enables the stimulation algorithm to "learn" the most efficient means of maintaining and optimising methane production through controlling the rate and composition of the nutrient mixture being dosed depending on the specific characteristics of a particular indigenous environment.

Preferably, the algorithm calculates the proportion of nutrients available to the microbial consortia in the indigenous environment. Preferably, the algorithm draws upon comparative data from different times, microbial consortia and/or carbonaceous material in determination of the desirable characteristics of the first, second and/or subsequent nutrient compositions. In a preferred embodiment, the carbonaceous material is coal and/or carbonaceous shale and the algorithm considers rock characteristics (including maceral composition) to determine the desirable characteristics of the first, second and/or subsequent nutrient compositions. Monitoring the microbial consortia environment preferably includes monitoring the generation of methane, for example, a reduction in the level/amount/volume of methane generated indicates that adjust to the indigenous microbial environment is required. In the broadest sense, this includes the monitoring of methane extracted from the production well. The monitoring of the methane generation is preferably designed to measure the amount of natural biogenic and enhanced biogenic production of methane. This may be performed through establishing a baseline of methane generation prior to the introduction of an initial nutrient composition. Similarly, observation of an inflection point with regard to a change from a maximum of methane generation to a steady reduction of methane generation is indicative that remedial action, such as further nutrient dosing, might be required to boost or enhance flagging biogenic methane production, although there is no reason why such action might be taken prior to the observation of the inflections point as the beneficial effect described would inherently occur, but the degree of resultant methane generation improvement would be less straightforward to quantify.

'Enhanced biogenic production of methane' may refer to increasing the volume of biogenic methane produced from the carbonaceous material in a given period relative to the volume of biogenic methane produced (natural production) from the carbonaceous material in the absence of the nutrient composition in the same period. Alternatively, 'enhancing biogenic production of methane' may refer to accelerating the rate of production of biogenic methane from the carbonaceous material relative to the rate of production of biogenic methane produced from the carbonaceous material in the absence of the nutrient combination. Thus an enhancement in biogenic production of methane can be identified by observation of increasing volume/rate and or amount of methane production from a well or field. Likewise observation of reducing volume/rate and or amount of methane production indicates reduction in performance signally remedial action must be taken to boost production.

In one embodiment, enhancing biogenic production of methane may be achieved by increasing the size of the methanogenic microbial consortia or by increasing the rate of methanogenesis in said microbial consortia.

The one or more methanogenic microbial consortia may be any microbial population capable of methanogenesis, in other words which is capable of degrading the carbonaceous material to produce methane or methane precursors such as hydrogen gas, carbon dioxide, acetates and other organic compounds such as formates, methanol and methylamines.

Said microbial consortia may be indigenous microbial populations which naturally occur or co-exist with the carbonaceous material.

Alternatively, or additionally, the methanogenic microbial populations may be introduced to the carbonaceous material. The introduced methanogenic microbial populations may be indigenous with respect to a separate or alternative carbonaceous material, including microbial populations derived from formation water in the same or neighbouring catchment areas.

Thus, in one embodiment, the nutrient composition further comprises one or more methanogenic microbial populations. More preferably, the one or more methanogenic microbial populations comprise microbes selected from the group consisting of Methanobacteria, Methanococci, Methanomicrobia, Methanopyri, and combinations of one or more thereof.

Alternatively, the introduced methanogenic microbial populations may be from a bioreactor or engineered microbial cultures.

Engineered microbial cultures include those produced through classical selection methods or other genetic modification methods. In some embodiments, utilisation of natural indigenous bacteria is preferred over genetically modified bacterial as introduction of same into the environment may be undesirable in certain locations.

In one embodiment, the one or more methanogenic microbial populations may be derived from, or may be found in certain formation water from, for example, water from coal bearing rock formations.

The formation water of the invention may be collected, and analysed in accordance the methodology described in U.S. Pat. No. 6,543,535, the relative parts of which are incorporated herein by reference, and in particular concerning the sections headed Step 1 describing 'Collecting Samples', Environmental Analysis, Microbial Analysis, etc. The teachings in this document provide the skilled person with sufficient information to allow formulation of suitable nutrient compositions for the specific microbes used/described herein.

In addition to the monitoring of methane formation, the monitoring preferably includes analysis of one or more parameters of the indigenous environment, including:
  formation water composition, pH and/or ionic strength/conductivity and/or specific density/turbidity/absorbance, temperature, pressure, etc;
  carbonaceous medium composition (e.g. N, P, S, O, C, H), including maceral composition; and
  microbial consortia analysis, including colony formation, strains/proportions of strains or other characterisation of methanogens, for example, metabolic by-products, etc;
  vitamins, trace elements and other nutrients; and
  methane generation/generation rate/levels of methane precursors, or in some cases, consumption of such precursors.

Preferably, at least two of the above parameters are monitored (e.g. formation water and carbonaceous medium composition), more preferably, at least three parameters and even more preferably, four or in some embodiments, all of the parameters are monitored. The greater the scope of parameters monitored the greater the understanding of the in situ indigenous environment, which thereby enables better management of the sustainable production of biogenic methane, and well as facilitating the accuracy/predictability of adaptive algorithm calculations.

In addition to the nutrients described above, the nutrient compositions of the invention may comprise any matter or environmental condition which stimulates the production of methane from the indigenous environment, either directly through stimulation of the microbial consortia or indirectly through modification of other parameters in the indigenous environment which ultimately lead to increased methane levels.

Accordingly, in various embodiments, the nutrient composition may further comprise at least one trace element selected from the group comprising iron, manganese, cobalt, zinc, molybdenum, nickel, aluminium, boron, copper, tungsten and selenium. The trace element may be present in the nutrient composition as an aqueous soluble salt thereof. The concentration of each trace element in the nutrient composition may be less than 200 ppm.

In other embodiments the nutrient composition may further comprise at least one vitamin selected from the group comprising pyridoxine, aminobenzoic acid, pantothenate, nicotinic acid, riboflavin, thiamine, thioctic acid, biotin, folic acid, pyruvate, and B12. The concentration of each vitamin in the nutrient composition may be less than 100 ppm.

In further embodiments the nutrient composition may further comprise at least one stimulant. Stimulants may be any factors that can be used to increase or stimulate the biogenic production of methane in the carbonaceous material. Examples of stimulants include, but are not limited to, yeast extract, Coenzyme M, lactic acid, mineral amendments (such as chloride, sodium, potassium, magnesium and calcium), alkyl alcohols, methanol, ethanol, 2-propanol, 2,3 butanediol, vanillate, glycine, cysteine, 3,4,5-trimethoxybezoate, cellulose, cinnamic acid, benzoic acid, chitin, chitosan, chlorate, perchlorate, and any combinations thereof.

Other additives may also be included in the nutrient composition for various purposes, for example, to stabilise the nutrient composition against deterioration over time and prolong shelf life, maintain constant pH, and so forth. Such additives may include, but are not limited to, acids, bases, buffering agents, oxidants, anti-oxidants, surfactants, emulsifying agents, gelling agents, any combination thereof and the like.

For the purposes of the present invention the term 'nutrient composition' preferably includes compositions which also stimulate growth or methane producing activity of the microbial consortia, or compositions comprising component whose metabolic products stimulate growth or methane producing activity of the microbial consortia. This may include compositions which alter the pH level or ionic strength, etc., of microbial consortia's environment.

The source of phosphorus in the nutrient composition may be any substance containing phosphorus in a form that is bioavailable to the one or more methanogenic microbial populations and has the effect of stimulating the biogenic production of methane. The method of determining whether a particular source of phosphorus has a stimulatory effect is well known to those skilled in the art.

In various embodiments, the source of phosphorus may be phosphorus containing compounds such as salts of phosphorus oxoacids, phospholipids or derivatives thereof, organophosphate esters, and any combination thereof and the like.

Examples of suitable salts of phosphorus oxoacids including, but not limited to, salts of hypophosphorus acid ($H_3PO_2$), phosphorus acid ($H_3PO_3$), metaphosphorus acid ($HPO_2$), orthophosphorus acid ($H_3PO_3$), metaphosphoric acids (($HPO_3$)$_n$), polyphosphoric acids (($HPO_3$)$_{n+2}$), tripolyphosphoric acid ($H_5P_3O_{10}$), pyrophosphoric acid ($H_4P_2O_7$), orthophosphoric acid ($H_3PO_4$), and the like.

Examples of suitable phospholipids include, but are not limited to, lecithin wet gum, lecithin, cephalin, phosphatidate, phosphatidylserine, phosphatidylinositol, phosphatidylinositol phosphate, phosphatidylinositol bisphosphate, phosphatidylinositol triphosphate, ceramide phosphorylcholine, ceramide phosphorylethanolamine, ceramide phosphorylglycerol, and the like.

Examples of suitable phospholipid derivatives include, but are not limited to, natural phospholipid derivatives found in eggs, soy, hydrogenated soy, or synthetic phospholipid derivatives of phosphatidic acid, phosphatidylcholine, phosphatidylglycerol, phosphatidylethanolamine, phosphatidylserine, PEG phospholipids, and the like.

Examples of suitable organophosphate esters include, but are not limited to, trixylenyl phosphate ester, butylated phenol phosphate ester, isopropyl phenol phosphate ester, and the like.

The source of nitrogen in the nutrient composition may be any substance containing nitrogen in a form that is bioavailable to the one or more methanogenic microbial populations.

In various embodiments, the source of nitrogen may be an inorganic nitrogen compound such as nitrogen hydrides and salts thereof, nitrogen oxoacids and salts thereof, urea, carbamide, hydroxylamine, ammonium chloride, sulfamide, thiocyanate salts, any combination thereof and the like. Examples of suitable nitrogen hydrides include, but are not limited to, ammonia, azanes such as hydrazine, triazane and so forth, diazene, trizene, and the like. Examples of suitable salts of nitrogen oxoacids include, but are not limited to, salts of hyponitrous acid ($H_2N_2O_2$), nitrous acid ($HNO_2$), nitroxyl (HNO), nitric acid ($HNO_3$), peroxynitrous acid ($HONO_2$), any combination thereof and the like.

In other embodiments, the source of nitrogen may be an organic nitrogen compound such as amines and ammonium salts thereof, amides, amino acids, peptides, oligopeptides, proteins, any combination thereof and the like.

In alternative embodiments, the source of nitrogen may be a nitrogen compound which is a gas phase at ambient temperature and pressure. Said gaseous nitrogen compounds may also be soluble in aqueous solutions at ambient temperature and pressure. Illustrative examples of such gaseous nitrogen compounds include ammonia, nitrogen, and nitrogen oxides. In particular when the nutrient composition may be employed to enhance methanogenic production of methane in subterranean formations bearing carbonaceous material, it is anticipated that the solubility of said gaseous nitrogen compounds in the nutrient composition is likely to increase in response to increased temperature and pressure in said subterranean formation.

It will be understood by the person skilled in the art that suitable sources of phosphorus or nitrogen may vary dependent upon the methanogenic microbial population and the carbonaceous material. The selection of suitable sources of phosphorous and nitrogen may be readily performed through a screening process in which the effectiveness of various nutrient compositions is tested upon specific carbonaceous material and methanogenic microbial populations.

The term 'carbonaceous medium' is broadly used to refer to any carbon-containing substance capable of supporting, and are preferably present or provided with, one or more methanogenic microbial populations. The carbonaceous material may be subject to degradation by said one or more methanogenic microbial populations to produce methane or methane precursors. Suitable examples of carbonaceous material include, but are not limited to, carbonaceous shale, coal, lignite, peat, drill cuttings, waste coal, coal derivatives, oil shale, oil deposits, tar sands, hydrocarbon-contaminated soil and petroleum sludges. The carbonaceous material preferably comprises at least 0.5 wt % N and more preferably at least 1.0 wt % N on a dry ash-free basis.

The terms "medium" and "material" are used interchangeable within the specification.

The carbonaceous material may be in-situ carbonaceous material or ex-situ carbonaceous material which has been removed from its natural/original location, for example, for processing and/or testing. In-situ carbonaceous material may refer to carbonaceous material residing in an original source location such as a subterranean formation, or goaf bearing carbonaceous material. Ex-situ may refer to a carbonaceous material that has been removed from its original source location as described herein. Ex-situ carbonaceous material may exist in a reactor, a bioreactor, a heaped pile and/or alternative above ground structures, a pit, and so forth.

International Publication WO2014/094055, incorporated by reference herein, describes a suitable initial nutrient dosing composition for enhancing biogenic methane production from a carbonaceous material, the nutrient composition comprising a source of phosphorus (P) and a source of nitrogen (N), wherein the molar ratio of phosphorus to nitrogen (P/N) is greater than 1.5, and the nitrogen concentration is at least 0.1 mM and less than 1.7 mM.

The relatively high ratio of phosphorus to nitrogen (P/N) in the nutrient composition is unexpected, particularly given that microbes are typically composed of more than about 10 fold more N relative to P. In some embodiments, the ratio of phosphorus to nitrogen (P/N) may be greater than 2. The ratio of phosphorus to nitrogen (P/N) may be less than 8.

The nutrient composition may comprise a nitrogen concentration of at least 0.2 mM. In one embodiment the nitrogen concentration may be less than 1.6 mM. In another embodiment the nitrogen concentration may be less than 1.5 mM. In another embodiment the nitrogen concentration may be less than 1.0 mM. In a further embodiment the nitrogen concentration may be less than 0.5 mM.

The nutrient composition may comprise a phosphorus concentration of at least 1.5 mM, preferably at least 1.7 mM and more preferably at least 2 mM.

In situ carbonaceous material may co-exist with associated water or formation water. Accordingly, it will be appreciated that in some embodiments the nutrient composition may undergo dilution with said associated water.

Accordingly, there is provided a concentrate for producing a nutrient composition, the concentrate being formulated to provide upon dilution with liquids associated with the carbonaceous material, a nutrient composition having an effective P/N molar ratio greater than 1.5, and an effective nitrogen concentration is at least 0.1 mM and less than 1.7 mM.

An effective P/N molar ratio is determined by the respective molar concentrations of phosphorus and nitrogen in any solution, emulsion, colloidal suspension, or gel that it is in contact with or proximal to the carbonaceous material. Similarly, an effective nitrogen concentration refers to the nitrogen concentration of any solution, emulsion colloidal suspension, or gel that is in contact with or proximal to the carbonaceous material. It will be understood that prior to coming into contact with or being disposed proximal to the carbonaceous material, such solutions, emulsions, colloidal suspensions, or gels may undergo dilution with fluids associated with said carbonaceous material in the course of being brought into contact therewith.

Thus in one embodiment a preferred initial biogenic methane production composition comprises a nutrient composition for enhancing biogenic methane from a carbonaceous material comprising a source of phosphorus (P) and a source of nitrogen (N), wherein the molar ratio of phosphorus to nitrogen P/N is greater than 1.5, and an effective nitrogen concentration is at least 0.1 mM and less than 1.7 mM.

It will be understood that the ratios and concentrations of phosphorus and nitrogen defined above are based on injecting the concentrate into an in situ carbonaceous material according to a plug flow model. It will be appreciated that other delivery models may be employed and consequently, the molar ratios and concentrations of phosphorus and nitrogen in the concentrate (and the nutrient composition) may vary depending on the various parameters and conditions of the delivery model.

Preferably, the nutrient composition is in intimate contact with the carbonaceous material to enable the nutrient composition to be readily available to the methanogenic microbial populations inhabited therein.

Preferably, contacting said nutrient composition with the carbonaceous material is achieved through mixing or agitating of the nutrient composition through existing environment proximate to the carbonaceous material (e.g. formation water).

Contacting the nutrient composition with the carbonaceous material may be achieved through adjusting the injection pressure of the nutrient composition into the carbonaceous material through know techniques available to those skilled in the relevant art.

In a preferred embodiment, contacting the nutrient composition with the carbonaceous material is achieved through sub-surface flow manipulation techniques, such as those disclosed in WO2011/017771, which is incorporated herein by reference.

Within this preferred embodiment, the first nutrient composition is thought to increase activity the microbial populations to an extent that the microbial population releases sufficient nitrogen within the carbonaceous material, such that additional nutritional supplements are effective in enhancing methane production with lower nitrogen concentrations or no nitrogen at all. The first nutrient composition may function to reactivate a relatively dormant microbial population, with the second nutrient composition supplementing the nutritional needs of a re-invigorated microbial population.

The time delay between the contacting of the first and second nutrient compositions with the carbonaceous material is preferably at least 1 week, more preferably at least one month and even more preferably at least two months. The maximum time delay between the contacting the first and second nutrient composition with the carbonaceous material is preferably less than one year and more preferably less than 6 months.

BRIEF DESCRIPTION OF THE DRAWINGS

FIG. 3(a) is a schematic diagram of a conventional dosing regimen, while

FIG. 5 is a 2D graph derived from data from the 3D graphs in FIG. 4 in which the source of phosphorous in the composition has a constant concentration of 1.90 mM $K_2HPO_4 \cdot 2H_2O$ and the concentration of the source of nitrogen (e.g. $NH_4Cl$) varies.

FIG. 6(a) is a photo of the vessels used to volumetrically measure the gas produced from cycle to cycle.

FIG. 6(b) is a photo of the capillary and burette arrangement used in the simulation/model experiments described herein.

DETAILED DESCRIPTION OF THE INVENTION

Theoretical Field Example

Figure 1:
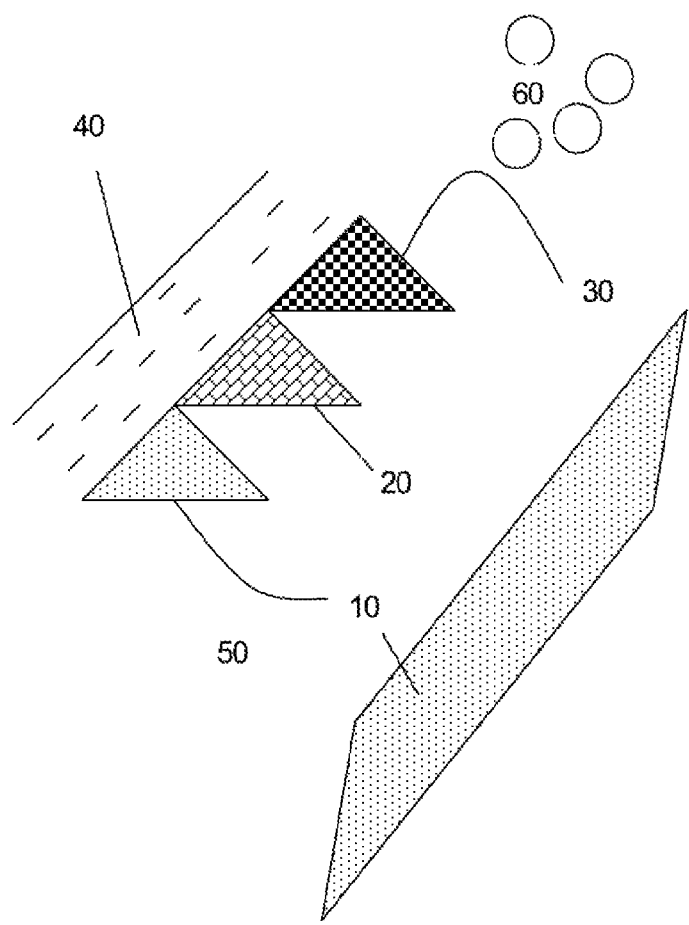
FIG. 1 is a schematic diagram of a subterranean formation of coal or carbonaceous shale containing formation water.

With reference to FIG. 1, there is illustrated a subterranean carbonaceous formation comprising coal or carbonaceous shale having a range of different areas of different maceral compositions (10, 20, 30 and 40) surrounded by formation water (50). The subterranean formation is characterised by natural macroscopic and microscopic fracturing or cleats which means that the formation system, including the cleats, fractures and pore spaces and surround rock formation are all surrounded by formation water. Accordingly these structures are wet structures, all of which are accessible by nutrient and other fluid compositions provided thereto. Thus, the formation itself serves a fluid (gas and liquid) reservoir, while the cleats/fractures in the formation allow the methane or other fluid to travel through the system to a wellbore. While methane is generally initially adsorbed onto the coal, know desorption processes can be used to free the methane and can typically involve lowering the water pressure in the target area. The permeability of the cleat and fracture formation allows these fluids to flow through the system.

Cleat formation is influenced by the maceral composition, with different maceral compositions affecting both endogenetic and exogenetic cleat formation. Different macerals have different chemical compositions and structural properties which impact on the ability of microbial consortia to access the nutritional requirements for sustained production of methane.

Examples of macerals include inertinite, vitrinite and liptinite.

Liptinite macerals originate from the waxy and resinous components of plants including leaf cuticles, spores, pollen and algal matter. Liptinite macerals tend to retain their original morphology and are hydrogen rich such that they have the highest hydrocarbon generation potential of all macerals. Individual macerals of the liptinite group are sporinite, cutinite, resinite, alginite (telalginite and lamalginite), suberinite, liptodetrinite, fluorinite, bituminite and bitumen/exsudatinite.

Vitrinite originates mainly from woody tissues of land plants, such as, roots, bark, stems and trunks. Most vitrinite undergoes gelification during burial such that original plant structures may become obscured. It has hydrogen contents (and hydrocarbon generation potential) intermediate to liptinite and inertinite. The vitrinite maceral group is divided into telovitrinite, detrovitrinite and gelovitrinite, largely on the basis of origin and morphology. Telovitrinite and detrovitrinite often occur interbanded or interlaminated with inertinite; vitrinite-rich bands and can be recognised in coal seams as 'bright' bands. Vitrinite macerals are the most prone to develop cleats.

Inertinite generally has similar origins to vitrinite except that it was charred before deposition or during the early stages of burial. It has the lowest hydrogen content of the maceral groups and therefore has the lowest hydrocarbon generation potential. Similar to the subdivisions of vitrinite, inertinite can be divided into telo-inertinite, detro-inertinite and gelo-inertinite.

To obtain the methane, wells are made by drilling down from the surface into the coal layers whereby the ensuing release of pressure causes methane desorption. Furthermore, pumping ground water or injection gases, such as $N_2$ or $CO_2$, around the system desorbs further methane causing the released gas to flow to the surface.

Figure 2:
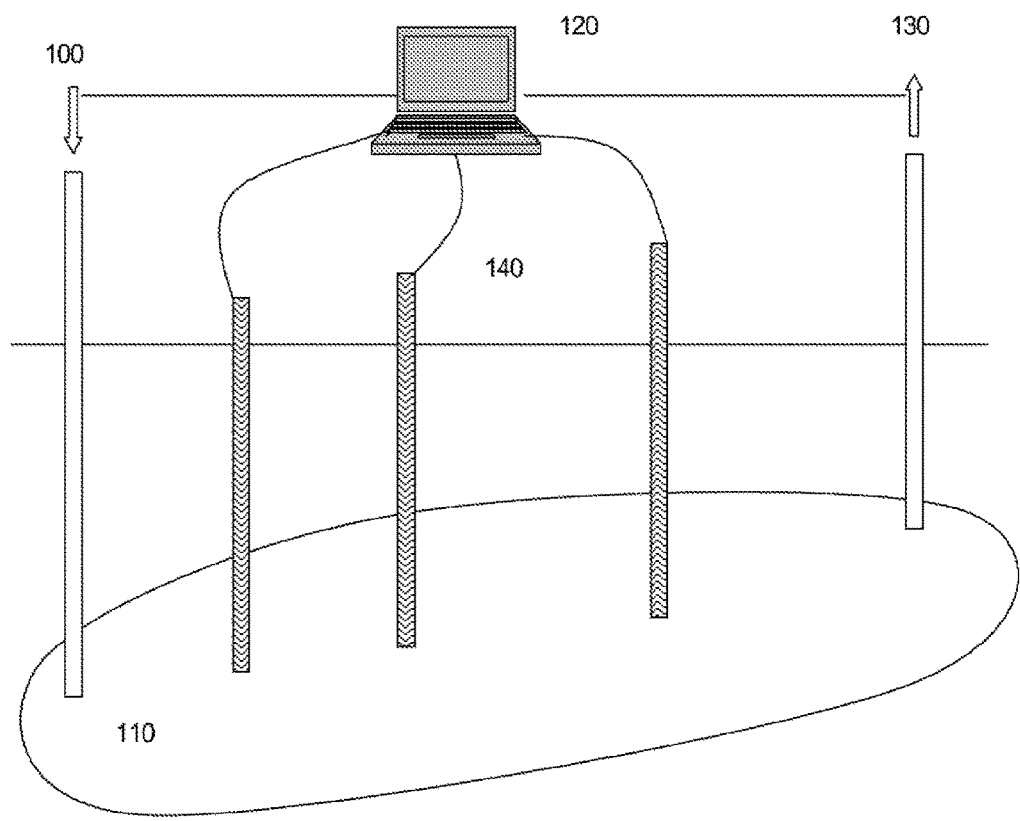
FIG. 2 is a schematic diagram of nutrient injection in a methane generating field in which the subterranean environment is monitored over time in accordance with the present invention.

When methane production from the well falls to undesirable levels, samples of the formation water in different areas around the formation ((140) in FIG. 2) can be taken and microbial presence/methane and other component levels/properties can be determined as described elsewhere herein. Geological studies to indentify prime areas of the formation for methane generation can be determined.

Depending on the characteristics observed, nutrient compositions of the invention, or exogenous formation water with active consortia or both, can be injected into the formation.

In either case, the formation water and/or composition and amount of nutrient required to stimulate methane production (60) from the microbial consortia (not shown) will be dependent upon the ability of the microbial consortia to derive nutrients from the indigenous environment (i.e. indigenous nutrients), including formation water (50) and the various carbonaceous material present, which will have various characteristics that impacting upon nutrient availability to the microbial consortia (10, 20, 30, 40).

The availability of indigenous nutrients to the microbial consortia will vary with time and will be dependent upon a number of factors including the changing nature of the microbial consortia, the formation water, and organic material present over time. The availability will also vary spatially naturally, with respect to amounts and types of macerals present, as well as the consumption action of the microbes over time.

Through surveying the rock characteristics, including maceral composition, formation water characteristics, etc., over a production field, variations in external nutritional requirements of the microbial consortia may be better controlled. Also, as the carbonaceous material is consumed in the production of methane, the nature of organic material present will also change as 'digestible' portions are consumed. As a result there is also a change over time in the indigenous nutrients available to the microbial consortia and efficiency of methane generation can alter.

For example, over time, a decrease in the proportion of nitrogenous components (10) combined with a rise in a low nitrogen components (40) in the field will result in an increased external nutrient, such as nitrogen, requirement, (with other nutrient components also being in excess or deficit to requirements). The imbalance of the total available nutrients is likely to reduce overall methane production rates, and if not rectified, the microbial consortia will decline and methane production will eventually completely cease or run to unrecoverable low levels.

The nitrogen content of macerals may vary from trace amount up to about 5 wt %, with variations between the highest and lowest nitrogen content being up to a tenfold or more, depending on the characteristics of a particular/given area.

The methodology of the present invention includes dosing a first nutrient composition (100) into a microbial consortia (110). Suitable injection process for dosing are described in U.S. Pat. No. 6,543,535 and US2011/025082, and include fluid (aqueous solution, gas, solvent or polymer) delivery, gas (e.g. $CO_2$) or waterflood delivery methods, or combinations of same, if appropriate.

The composition of the initial nutrient composition is preferably determined by analysing the characteristics of the indigenous environment, including the type and/or amount of carbonaceous material, the formation water and/or the microbial consortia present. As mentioned earlier, suitable analytical techniques for determining the requirements/composition of the first nutritional composition may be found in U.S. Pat. No. 6,543,535 and US2011/025082.

After the initial dosing of the exogenous formation water and/or the nutrient composition described herein, the reservoir/coal bed (110) can be monitored for methane production through the use of sensors or sampling points (140). Other environmental conditions, for example, salinity, pH, etc may also be monitored and adjusted at this stage if appropriate. Suitable adjustment methods for these properties are described in U.S. Pat. No. 6,543,535 and changes can be by injection of fluids (e.g. water, solvent, and polymer) or gases as part of the secondary or tertiary recovery process. One example in U.S. Pat. No. 6,543,535 includes provision of fluids of adjusting salinity, and/or temperature.

During this initial dosing phase (commission phase), the amount of nutrient dosed may be further adjusted to ensure that methane production rates fall within and/or are maintained within expectations. Within coal or carbonaceous shale deposits, the external nutrient composition dosed into the coal bed will typically be allowed to stimulate the microbial consortia over a period of time which may range from about 1 month to 12 months after which methane extraction occurs through a production well (130). In laboratory stimulation experiments, the incubation range can be from 1 week onwards, whereas sampling interval can be continuous or can be selected on the basis of the type of analytical equipment available.

When a suitable incubation period has elapsed, the methane is preferably extracted/recovered from the coal bed at a sustainable rate, via known extraction methods. Recovery of methane produced by the microbial activity can be by any suitable gas production technology, a number of which are described in U.S. Pat. No. 6,543,535.

The formation can then be dosed with further exogenous formation water and/or the nutrient composition and sealed if necessary to allow re-incubation for a second and/or subsequent cycle.

Ideally, a suitable dosing regimen can be devised (for example, see FIGS. 3(a) to 3(e), such that the rate of methane formation by the microbial consortia will match the methane extracted from the well.

In an alternative embodiment, the methane can be extracted continuously until the methane production level drops to a pre-determined amount (e.g. 70% or 50% below peak methane production rate or as described above), after which the production well will be capped and further dosing of nutrients is commenced and the dosing/methane recovery cycle continued.

As shown schematically in FIG. 2, the sustainability of the methane recovery (either continuously or periodically) will be monitored by sensors or samples removed from the field for testing/analysis/monitoring (140). Ideally, a computer (120) will be used to analyse data relating to the input of nutrients; the indigenous environment and changes thereto, and the methane recovery rates/levels/amounts. Through analysis of the input data, a computer simulation model of the indigenous environment can be formed. The model using variations in indigenous environment, combined with variations in external nutrient dosing will be able to predicatively respond to detected changes in the indigenous environment by adjusting the rate and composition of external nutrients accordingly to maintain a sustainable rate of methane production.

The stimulation model preferably will take inputs from multiple samples from a plurality of locations within the methane catchment area. Through taking multiple samples within the catchment area the stimulating model will be more reflective of the indigenous environment, with the stimulation model being based upon multiple input data relating to variations in maceral composition, formation water composition and microbial consortia composition at various locations over different time intervals, thereby providing a dynamic stimulation model in which detected variations in the indigenous environment location may be responded to by using the data (i.e. learning) from a different indigenous environment location and/or time. Details of a number of means for sampling are described in U.S. Pat. No. 6,543,535 whereby samples can be obtained from the formation through one or more wells in communication with the formation, such that the concentration and type of microorganisms in the fluid as well as the concentration of stimulants and microbial products in the fluid can be assessed. As described in U.S. Pat. No. 6,543,535, other geochemical analyses may also be performed to assess the effectiveness of the stimulants on the formation environment.

In a preferred embodiment, sensors will be used to monitor the indigenous environment with automated sensors, for example, sensors capable of monitoring the environmental or gas production parameters described herein, will be used to monitor the indigenous environment. The ability to provide data on the indigenous environment at small time intervals, for example, achievable via use of inline, substantially continuous monitoring, will increase the robustness and/or adaptability of the stimulation model.

Alternatively and/or in addition to, regular sampling of the catchment area may be employed to provide additional data and to calibrate sensors, where required. Sampling intervals will typically vary from substantially continuously, to sampling over a set second, minute, hourly, daily, weekly, fortnightly, monthly or yearly interval.

In one embodiment, for example, involving laboratory simulation or modelling, the sampling interval can be based shortly scale, for example, over a set second, minute, hourly, daily, weekly, fortnightly, monthly interval. However, in the field, longer sampling periods may be sufficient for example, weekly to 6 monthly, with sampling at least every 1 to 3 months preferred. The optimum sampling period within a given incubation period will depend on the dynamics of a given formation/field. More rapidly changing environments will benefit from more frequent sampling, while conversely, slower changing environments can be sampled less frequently. Sampling frequency may also be determined in accordance in a way that is most economical sensible for a particular sensing method used, however, in general it would be desirable to sample as frequently as possible.

Through better understanding the interaction of the formation water, the carbonaceous medium, the microbial consortia, including their inputs and outputs, dosing regimen will become optimised to the specific requirements of a given methane producing catchment area. In addition to changes in the nutrient composition, the analysis of the indigenous environment may lead to a dosage regimen which varies the amount and frequency of the external nutrient composition to heighten microbial activity.

Figure 3A:
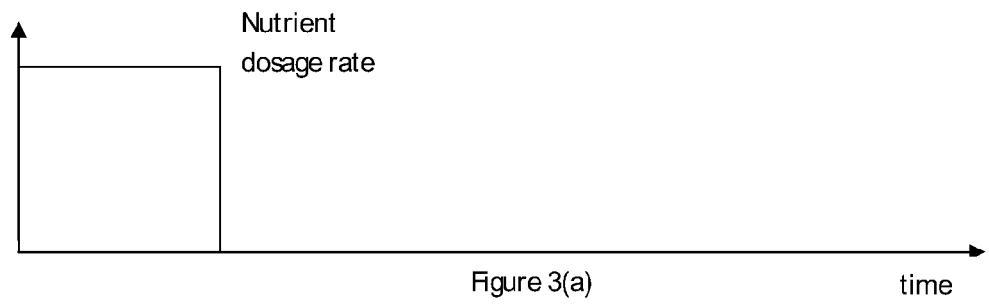
Figure 3B:
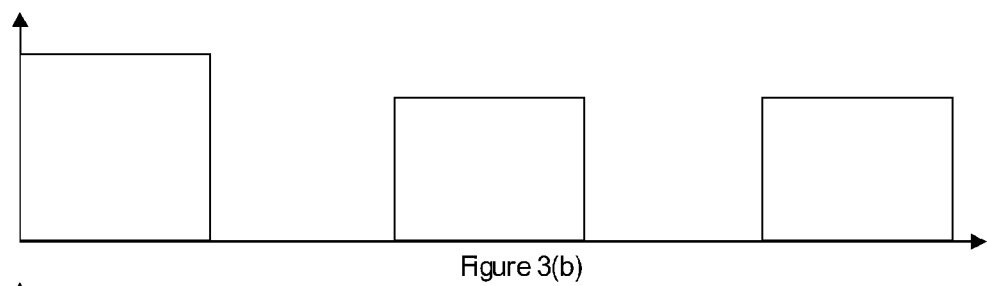
FIGS. 3(b) to 3(e) are dosing regimens under the scope of the present invention.
Figure 3C:
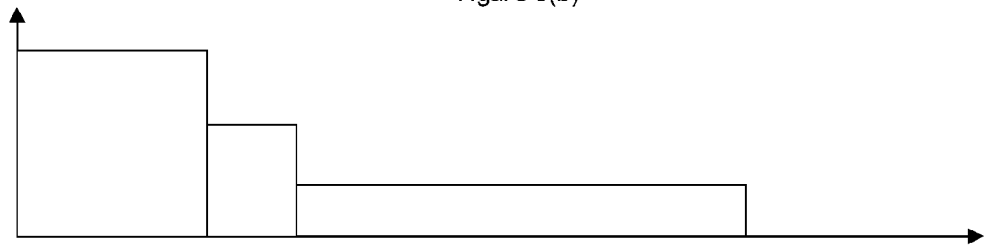
Figure 3D:
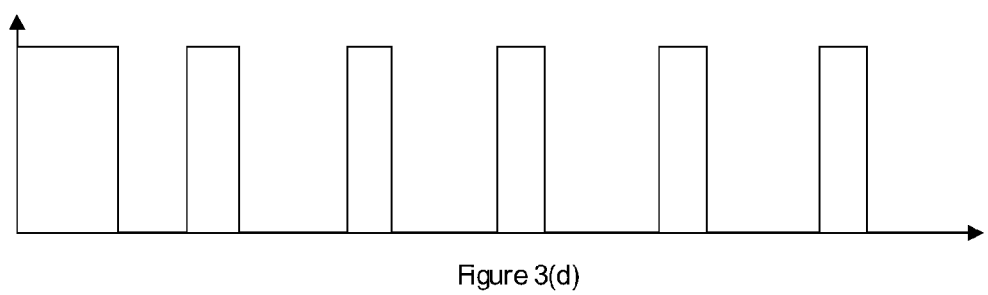
Figure 3E:
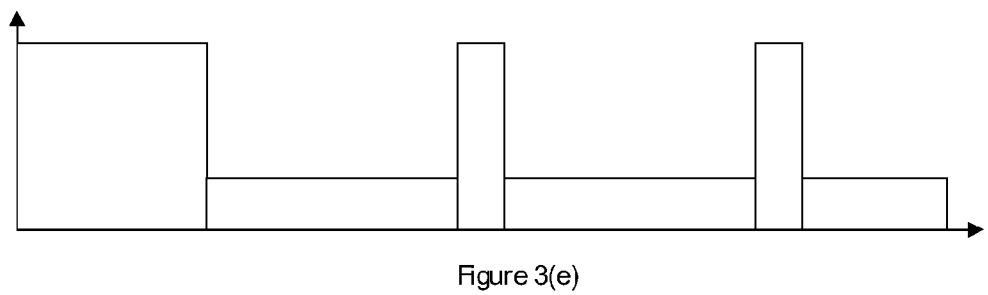

FIGS. 3(b) to (d) provide examples of potential dosing regimen gained through the use of the process of the present invention. The appropriate dosing regimen to a specific catchment area may be selected depending upon the output of the monitoring of the indigenous environment over time.

Suitable analytical techniques for the analysis of coal include: ASTM D2799-13: Standard test method for microscopical determination of the maceral composition of coal; ASTM 2798: Test method for microscopical determination of the vitrinite reflectance of coal; ASTM: Test Methods for Total Sulfur in the Analysis Sample of Coal and Coke; Standards Association of Australia (1998). In AS 2856.2-1998 (R2013) Coal petrography—Maceral analysis, 35 pp; Standards Association of Australia. (2000a). In AS 2856.3-2000 Coal Petrography Method for Microscopical Determination of the Reflectance of Coal Macerals 22 pp and also for proximate and elemental analyses; Australian Standards AS 1038.1, AS 1038.3, AS 1038.6.1, AS 1038.6.2, AS 1038.6.3.3 and AS 1038.11, as of which are incorporated herein by reference. Microbial analysis and/or characterisation can be carried out using known DNA techniques. U.S. Pat. No. 6,543,535 provides a description of a number of suitable identification/characterisation methods.

In additional to a regular monitoring regimen, test nutrient packages may be dosed into the coal bed catchment area to assess the effects of various nutritional constraints on methane production and/or microbial consortia populations. The effect of one or more stimuli at one or more locations in the catchment area may be used to assess changes in formation water, (composition and dispersion through the catchment area) and/or changes in methane production and/or the microbial consortia which can be added to the stimulation model database.

In one embodiment, the present invention allows for cultivation of the indigenous environment through transferring a portion of, for example, a productive formation water (and microbial consortia therein) or other nutrients/components, to one or more different locations in the catchment area. In particular, the transfer of formation water comprising active consortia to different locations may be an effective means to favourably modify a local indigenous environment (e.g. transfer of a microbial consortia that is more tolerant to sulphur to a location experiencing an increased level of sulphur, or the like).

System for Enhancing Biogenic Methane Production

The biogenic methane production system of the invention comprises:
- one or more nutrient compositions as described herein;
- a delivery system for dispersing said nutrient compositions throughout the carbonaceous medium;
- a means for collecting/recovering methane from the carbonaceous medium/material; and
- a means for monitoring/detecting changes/variation in the microbial consortia environment, including the formation of methane therein.

Delivery System for Dispersing Said Nutrient Combination Throughout the Carbonaceous Material It will be appreciated by persons skilled in the art that the delivery system for dispersing the nutrient combination throughout the carbonaceous material will depend on whether the carbonaceous material may be an in situ carbonaceous material or an ex situ carbonaceous material.

Preferably the delivery system is an anoxic delivery system, as in some embodiments, oxygen can hinder or adversely affect the methanogenesis of certain bacteria consortia of the invention.

The delivery system for dispersing the nutrient composition throughout an in situ carbonaceous material may comprise an injection system for injecting the nutrient combination into, or proximal to, the in situ carbonaceous material. As discussed above in the context of the disclosure of U.S. Pat. No. 6,543,535, such systems are well understood by those skilled in the art of recovering CSM and may include, but are not limited to, injection under pressure, by gravity forces, other water injection methods, combinations of same, and the like. In some embodiments, such systems may be adapted to co-inject the nutrient combination with a further injection fluid, such as a hydraulic fracturing fluid.

Collector for Collecting Methane

It will be appreciated by persons skilled in the art that the collector for collecting the methane will depend on whether the carbonaceous material may be an in situ carbonaceous material or an ex situ carbonaceous material.

In respect of in situ carbonaceous material, the collector for collecting methane are well understood by those skilled in the art of recovering coal seam methane (CSM) and other carbonaceous material bearing subterranean formations. For example, recovery wells may be drilled to recover methane from the in situ carbonaceous material. The recovery well may be in fluid communication with a compressor to compress the recovered methane, and a storage reservoir or transport conduit for natural gas distribution.

It will be appreciated that the geometry of injection sites, laterals and recovery wells can be variable, but must be based on local geologic, structural, and hydrologic conditions in order to maximise the injection volumes of nutrient combination (concentrate) and to attain maximum recovery of methane. Additionally, at some point in time, the carbonaceous material between the injection sites or laterals and the recovery wells may become methanogenically unproductive. Subsequently, the recovery wells may be converted into injection sites and a new series of recovery wells may be drilled.

Sampling and gas compositional analysis can be performed easily by measuring a volume of gas evolved and sampling same for gas component presence using a suitable analytical technique, for example, GC analysis. However, the number of sampling points available can be limited to the evolution of a certain minimum level of evolved gas. Therefore, in preferred embodiments, sensitive inline gas compositional sensors can be used to continuously monitor the gas composition of any evolved gases. For example, infrared, semiconductor based, ultrasonic based, or electrochemical based gas sensors can be used. Electrochemical based gas sensors that measure concentrations of a target gas by oxidising or reducing the gas at an electrode and measuring the resulting current are particular preferred. Use of the latter is particularly desirable since rapid changes in methane generation rates can quickly be detected, allowing better remedial reaction times and more controlled over the system.

Experimental Rig

FIG. 6(a) shows the vessels used to volumetrically measure the gas produced from cycle to cycle, as well as the capillary and burette arrangement used in the simulation/model experiments described herein. This arrangement provides a custom gas sealing/sampling system designed to allow anaerobic sealing of the culture and still allow gas sampling and nutrient injection without causing microleaks which can occur with rubber septa by repeated perforations with gas sampling needles+syringes. In particular, the custom gas sealing/sampling system shown in FIG. 6(b) is used volumetrically measure evolved gas. The system consists of a 5 mL burette sealed at one end with a ¼" compression fitting at the other end utilising a PTFE ferrule and a septa sealing system, two 1/32" stainless steel needles, 1/32" FEP tubing and gas tight syringes. By adjusting the length of the two capillaries, one can displace all the air in the burette with water which then allows subsequent displacement by evolved gas from the gas culturing bottles. By careful maintenance of hydraulic head pressure, the gas from the culturing bottles can be volumetrically expanded to atmospheric pressure, allowing the volume of evolved gas at room temperature and pressure (RTP) to be determined while still allowing for subsequent gas analysis for bulk composition by MicroGC.

Calculation of Peak Rate of Methane Generation

The maximum/peak rate of methane generation and/or the maximum/peak rate of methane generation per unit nutrient provided, for example, per unit nitrogen dose, over a given incubation can be calculated from average over certain sampling interval during that incubation period, for example, a particular number of days, may be determined as follows:

Firstly, the average rate of methane generation over a given period is calculated to provide the average daily rate of methane generation.

The average daily rate of methane generation can be determined by considering the volume of methane gas recovered from a gas samples collected over a given sampling period throughout the incubation period. For example, if 30 cm$^3$ sample of gas is collected over a 6 day incubation/sampling period, the average daily rate of gas production corresponds to 5 cm$^3$/day (30 cm$^3$/6 days).

The corresponding average daily rate of methane generation can then be calculated using the % methane gas composition value for each interval which is typically established using, for example, GC analysis or gas sensor analysis. Thus, the collected gas sample over the interval concerned comprises, for example, 5.2% of methane, the average daily rate of methane generation would be 0.26 cm$^3$ methane/day. Thus, the peak rate of methane generated over a particular incubation period can be determined by comparing the range of average daily methane generation rate of the sampling intervals taken during that incubation period. The observable peak methane generation rate corresponds to the maximum average daily rate of methane generation calculated for any given sampling interval whereby gas is collected over a number of days as described herein.

In embodiments where a known concentration of nutrient is dosed into an indigenous microbial consortia, for example, 50 mg/L of NH$_4$Cl, the average daily rate of methane generation per unit of nitrogen can be calculated. In this case, the average daily rate of methane generation per unit of nitrogen would be 0.0052 cm$^3$ methane·day$^{-1}$·mg L$^{-1}$. (It will be understood that, where used herein, unless explicitly expressed otherwise, a concentration of N in mg/L means NH$_4$Cl.)

Calculating Peak Methane Gas Generation Rate Per Unit Nitrogen

For example, considering an extract from the table, below which includes a column for methane gas rate per day, it can be seen that the peak methane gas production mate and the corresponding peak methane gas generation rate per unit nitrogen for any given incubation cycle can be calculated. Thus, variations in peak methane gas generation rate per unit nitrogen can be easily observed between incubation/dosing cycles.

|  | Days (since last gas release) | N Dose (mg/L) | Vol. mls | Gas Rate mls/day | CH$_4$ (%) | methane gas rate mls · day$^{-1}$ | CH$_3$ rate/unit unit mg N |
|---|---|---|---|---|---|---|---|
| Days since start/initial dose | Initial dose | | | | | | |
| 0 | 0 | 100 | 0 | 0.0 | 0 | 5 | 0 |
| 16 | 16 | — | 23.6 | 1.5(1.475) | 5.5186 | 0.0024 | 0.00081399 |
| 24 | 9 | — | 8.8 | 1.0(0.977) | 5.2731 | 0.4368 | 0.00051518 |
| End first incubation period | | | | | | | |
| Days since 2$^{nd}$ dose | 2$^{nd}$ dose | | | | | | |
| 0 | 0 | 75 | 0 | 0.0 | | | |
| 14 | 14 | — | 19.5 | 1.393 | 5.2900 | 0.0737 | 0.0009625 |
| 24 | 10 | — | 15.0 | 1.50 | 5.405 | 0.0611 | 0.0010810 |
| 32 | 8 | — | 8.5 | 1.06 | 5.153 | 0.0548 | 0.0007300 |
| 43 | 11 | — | 4.8 | 0.44 | 4.5988 | 0.0201 | 0.0026756 |
| End second incubation period | | | | | | | |

Calculation of Peak Rate of Methane Generation

As can been seen below, the improved efficiency going to a lower dose of N in the second cycle is demonstrated by considering the number of moles of methane present per unit volume for various samples collected during first and second cycles. It is clear that the moles of methane per volume generated for both samples in the second cycle is greater than that observed for either samples taken from the first cycle at 100 mg/L nitrogen component. Furthermore, since the final sample parameter is increased on the previous sample, it Is clear that the system is still increasing in efficiency.

| Days (since last gas release) | Volume of gas evolved at RTP (21° C., 1 atm pressure) (cm³) | Gas Rate of CH₄ (mol/day since last gas release) | P Dose (mg/L) | N Dose (mg/L) | CH₄ (%) | Moles of CH₄ at RTP (mol) | mMole | mMole · cm⁻³ |
|---|---|---|---|---|---|---|---|---|
| Initial dose | 0 | 0 | 400 | 100 | | | | |
| 16 | 23.6 | 3.37E−06 | — | — | 5.5186 | 5.40E−05 | 0.005395784 | 0.0002286349 |
| 9 | 8.8 | 2.14E−06 | — | — | 5.2731 | 1.92E−05 | 0.001922482 | 0.0002164639 |
| 2$^{nd}$ dose | 0 | 0 | 400 | 50 | | | | |
| 12 | 4.76 | 9.63E−07 | | | 5.8591 | 1.16E−05 | 0.001155451 | 0.0002427418 |
| 15 | 4.86 | 1.06E−06 | | | 7.933 | 1.59E−05 | 0.001589657 | 0.0003270600 |

Mole calculated based on Ideal Gas Equation: $PV = nRT$, $n = (PV)/(RT)$, $R = 8.3144621 \times 10^3$ cm³ kPa K⁻¹ mol⁻¹;
1 atm = 101.32501 kPa;
Pressure = kPa;
Volume = cm³, but since gas species not 100% must allow for % composition.
Temperature = absolute = 273.15 + °C. = K;
Lab Temp = 21° C. = 294.15K Continuous Methane Monitoring—Inline Gas Sensor An automated inline sensor will, calculate the methane concentration over a plurality of sample points thereby improving accuracy and potential for responsiveness to adverse changes in the system performance.

| Initial cycle | | | |
|---|---|---|---|
| Sample | P dose (mg/L) | N Dose (mg/L) | CH₄ (%) |
| 100 | 400 | 100 | 0 |
| 200 | — | — | 5.5186 |
| 300 | — | — | 5.2731 |
| 400 | — | — | 5.8591 |
| 500 | — | — | 6.564 |
| 600 | — | — | 7.933 |
| 700 | — | — | 7.500 |
| 800 | — | — | 7.122 |
| 900 | — | — | 5.455 |
| 1000 | — | — | 5.002 |
| 1100 | — | — | 4.300 |

| Second cycle | | | | |
|---|---|---|---|---|
| Sample | P Dose (mg/L) | N Dose (mg/L) | CH₄ (%) | Expexted |
| 100 | 400 | 50 | 0 | |
| 200 | — | — | 5.112 | |
| 300 | — | — | 5.247 | |
| 400 | — | — | 5.450 | |
| 500 | — | — | 7.838 | |
| 600 | — | — | 8.243 | 3.967 (107.8%↑) |
| 700 | — | — | 5.998 | |
| 800 | — | — | 4.411 | |
| 900 | — | — | 4.003 | |
| 100 | — | — | 3.121 | |
| 110 | — | — | 2.115 | |

In the present case, the expected maximum for the second cycle would have been predicted as 50% of the first maximum since half the quantity of nitrogen component is used the second base. In this theoretical example, more than double the amount methane is formed.

Collecting Methane

It will be appreciated by persons skilled in the art that the manner for collecting the methane will depend on whether the carbonaceous material may be an in situ carbonaceous material or an ex situ carbonaceous material.

In respect of in situ carbonaceous material, the techniques for collecting methane are well understood by those skilled in the art of recovering coals m methane and associated gas from various recovery wells of oil and gas bearing subterranean formations. For example, to extract the gas, a steel-encased hole may be drilled into the coal seam (100-1500 meters below ground). As the pressure within the coal seam declines due to natural production or the pumping of water from the coalbed, both as and 'produced water' come to the surface through tubing. Then the gas is sent to a compressor station and into natural gas pipelines. Similarly, in respect of ex situ carbonaceous material, the techniques for collecting methane are well understood by those skilled in the art of recovering biogas from reactors, bioreactors, heaped piles and so forth. For example, the ex situ carbonaceous material may be confined in a closed space to retain the biogenic methane in a headspace thereof. The closed space may be defined by a shell disposed over the ex situ carbonaceous material, or any suitable covering such as a tarpaulin. The methane may be withdrawn from the headspace under positive or negative pressure.

Experimental for Simulation/Modelling Studies Including Theoretical Examples

Methanogenic Samples

Microbial consortium 1 was obtained from a coal-seam formation water from Sydney Basin NSW. One large volume sample was collected in a plastic carboy, shipped to the lab, filter sterilised and used as medium, inoculum was collected on site and immediately degassed by bubbling helium through it, followed by the addition of Na₂S to retain the reducing conditions. After shipping to the lab, this was stored anoxically and used as the microbiological inoculum for experiments. The coal used as feedstock was a Surat Basin coal of sub-bituminous maturity, and from around 500 to 700 meters subsurface.

Consortium 1: Is from formation water taken from a location in Queensland, Australia. This consortium is growing on a coal from this location. The consortium is growing at 40° C.

Consortium 2: Is from formation water from a location in NSW. This consortium is growing on a coal from this location (on which similar consortia have previously been shown to produce methane). The consortium is growing at 30° C.

The consortia are strictly anaerobic, and typically include a range of bacteria and archaeal, most commonly from the phyla: Firmicutes, Proteobacteria (Bacteria) and Euryarchaeota (Archaea) though numerous other phyla are present.

Microcosm Cultures—Serial Single Vessel Experiments

Simulation Rig

The inventors have custom built the valve sealing system shown in FIG. 7 such that it fits a 500 ml Schott bottle (see FIG. 6) to allow use as an anaerobic incubator bottle. The system allows the bottle/reactor vessel to be charged with nutrients and methanogens so that the experiments can be carried out anoxically. The system allows pressure to be released periodically, for example, over 1 week via capillary tubing so that the gas volume evolved can be measured in a volumetric pipette inverted in a water bath within an anaerobic chamber. After the gas volume has been measured, the gas can be then transferred to a gas tight syringe so that a gas compositional analysis can be run to quantify any methane present.

Typically, in these simulations, a week or so is required to allow build up of the minimum 5 mls of gas required for analysis. In some cases, 4-6 weeks are required for incubation before the bacteria produce significant levels of methane gas.

Formation water was sourced from the location for Consortium 1. This starting formation water was very productive, and was not been subject to freezing nor did addition of N or P containing component.

On day 14, the volume of produced gas was measured, and the gas composition was analysed with respect to methane, carbon dioxide, nitrogen, argon and hydrogen content. A minimum of 5 mls of gas is required for compositional analysis using the experimental set up designed herein.

The culture was then redosed with the same nutrients, however, at a reduced N concentration of 50/400 and remeasured.

To examine the effects of reduced nitrogen dosing levels, in a single anoxic vessel/chamber, 500 ml vials that included 200 ml formation water with 100 g of Surat coalgrain size (<1.2 mm>5.cm). Finally 2 mL of Consortium 1 was added as inoculant.

Media were reduced with the addition of 0.25 ml/l of a 200 mg/7 mL solution of $Na_2S.9_2O$. The headspace gas mixture in these vials was initially ~100% argon. Ammonium and phosphate nutrients were added to vials in the form of ammonium ($NH_4Cl$) and phosphate ($K_2HPO_4.2H_2O$) in varying concentrations depending on the dosage regime being considered, but starting with the nitrogen and phosphorus concentrations described in Table 1, to provide a time=0 day timepoint/baseline ratio of peak methane generation rate per unit nitrogen for cycle 1.

For example, for the initial dose, the culture was established with a nutrient composition comprising 100/400 mg $L^{-1}$ of $NH_4Cl/K_2HPO_4$ respectively.

After nutrient composition addition, the flasks were sealed with butyl-rubber septa and aluminium crimps (Grace Davison Discovery Sciences, Illinois, USA) and removed from the anoxic glove box. Cultures were inverted and incubated in the dark at 42° C. Culture vials were incubated in an inverted position to minimise loss of generated gases through the butyl rubber septa.

The length of the stimulation is variable. Broadly speaking, however, maximum concentration of methane appears to occur after 4 weeks, but before 8 weeks. In the present case, stimulation proceeded for as shown in the tables provided herein, although the inventors have found in some stimulation tests that certain cultures are capable of still producing methane at 18 months from a single initial nutrient addition.

In the present case, gas chromatography (GC) measurements of methane present in the gas volume tested were undertaken at regular intervals as shown. After sampling, vials re-gassed with 100% helium after sampling and collection was recommenced and the system allowed to rest for a minimum of 2 weeks before resampling.

Evolved Gas Measurement

Five ml gas samples were collected from septum sealed bottles via a gas-tight syringe. The composition of the culture gases were analysed on the Micro-GC. Samples were injected into the front injection port of the GC by syringe pump. The Micro-GC is equipped with three different column modules: 10 m Molsieve 5A column with backflush, a 10 m Pora Plot Q column with backflush and a 10 m CP-SN-5CB column. Gases were detected using a micro machined thermal conductivity detector for each module; limit of detection is in the order of ~1 ppm. The injector has a built-in 10 µl sample loop and the helium carrier pressure was set to 15 psi and the injector temperature was 90° C. The temperature of the Molsieve 5A column in channel 1, the Pora Plot Q column in channel 2 and the CP-SN-5CB column in channel 3 was set to 90° C., 70° C. and 60° C., respectively. After being injected into Micro-GC, gases are drawn by a vacuum pump through the sample loop and then the inlet system injects the gas sample from the sample loop into the carrier gas stream. $O_2/Ar$, $N_2$, $CH_4$ and CO are separated on the Molsieve 5A column. $CO_2$, $C_2H_6$ and $C_3H_8$ are separated on the Pora Plot Q column. $C_4$-$C_5$ hydrocarbon gases and $H_2S$ are separated on the CP-SN-5CB column. $O_2/Ar$, $N_2$, $CH_4$ and $CO_2$ amounts were quantified.

The results are provided in Table 1, together with number of theoretic examples based on the simulation/model system described herein.

It is noteworthy, that under experimental conditions unpredictable results can be obtained for one or more of the following reasons: gas productivity of cultures in the lab is unpredictable, some cultures produce only briefly, others produce for very long durations. This is true even for replicates. Therefore, since the tests have at least a degree of inherent variability, testing should be completed considering an average of a statistically relevant number of tests.

Initial Nitrogen (N) and Phosphorus (P) Inputs

It is surprising that relatively little N compared to P is required to produce optimal yields of methane. It is well established that the macro-chemical composition of "typical" bacteria and archaea are in the molar ratio range (C:N:P) 102:12:1 or in the case of P depleted conditions 259:69:1 (Cotner et al 2010). That is, the amount of N in a microorganism exceeds the amount of P by more than a factor of 10 even under P replete conditions. Hence, it would have been expected that more N than P may have been required for optimal growth of microbes and production of methane. Thus the present findings are counterintuitive.

Figure 4:
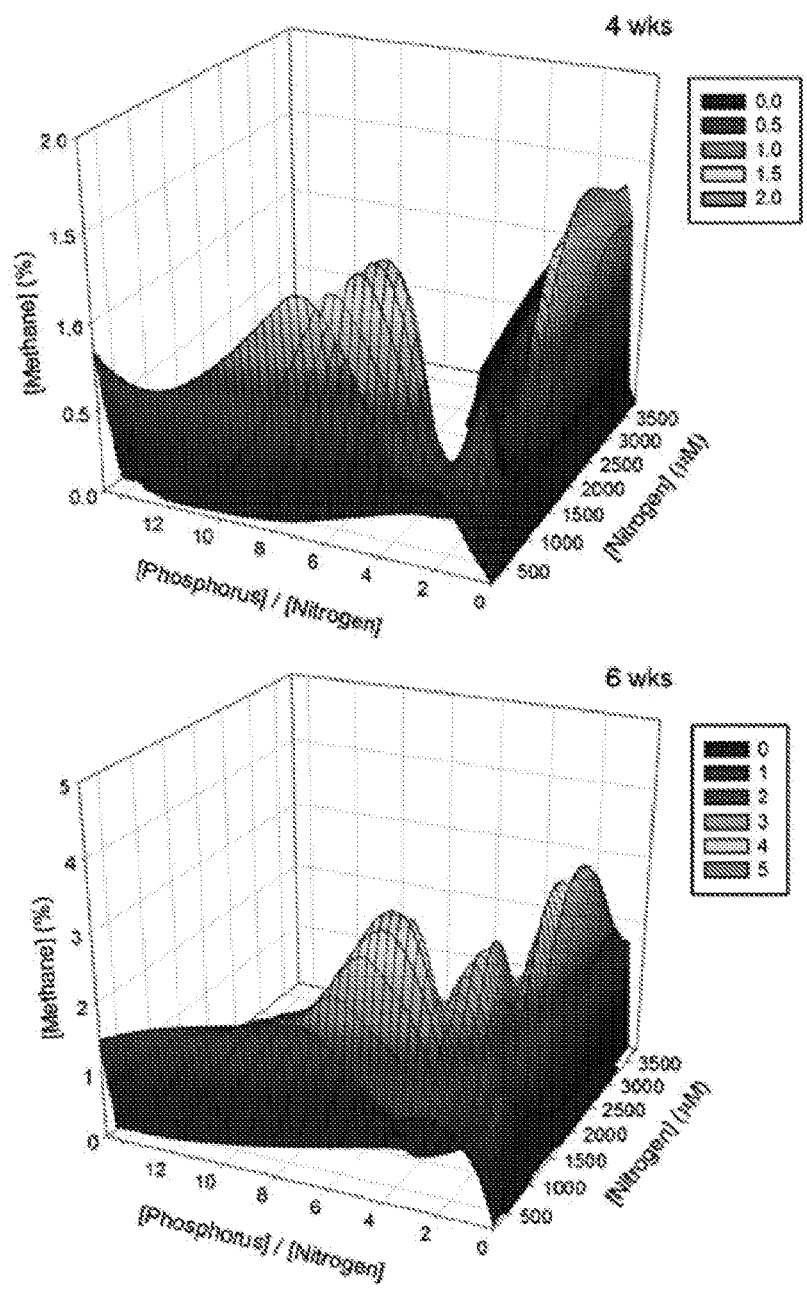
FIG. 4 is a 3D-interpolated mesh plot showing the effect of phosphorus to nitrogen ratio and nitrogen concentration in the nutrient composition on methanogenesis (as % methane in the headspace) of Surat coal by the Surat formation water consortium after four and six weeks incubation. The scatterplot data are smoothed in SigmaPlot v. 1 1.0 using a LOESS regression algorithm and an irregular mesh fitted to the shape.

As shown in FIG. 5, a 2D graph derived from data from the 3D graphs in FIG. 4 in which the source of phosphorous in the composition has a constant concentration of 1.90 mM P, the concentration of the source of nitrogen varies. The results indicate that the production of methane declines if the concentration of nitrogen in the nutrient composition exceeds 1.7 mM.

Results and Discussion

It has been surprisingly found that lower dosage of nitrogen in a second and/or subsequent dosing cycle increases the efficiency of methane production in a methanogenic bacterial consortia. This is indicated in FIG. 5 which highlights that at the 1.88 mM dose, $CH_4$ generation is lower than for the case where 0.47 mM NI is used.

The experiments described herein indicate that a simulated methanogenesis model, dosed with a nutrient composition with reduced a nitrogen dosage, performed better than when dosed with a repeated nitrogen level in the second dosage. In the latter case, where a higher nitrogen content was utilised, the model did not produce any methane.

These results are consistent with observations arising from previous methane production studies, results of which are provided in FIGS. 4 & 5. FIG. 4 demonstrates that methane production peaks at high and low level nitrogen additions indicating stimulation of bacteria with a nutrient composition at an initial high nitrogen dose, followed by a lower nitrogen dose is beneficial for increasing the efficiency of methane production per unit input of nitrogen. This is a surprising because intuitively, the skilled person would expect that failing methanogenesis would benefit from higher levels of nutrient supply, especially nitrogen. The findings are desirable since less than expected nutrient levels, such as nitrogen levels, are required for second and/or subsequent doses. The benefits of reduced nutrients include reduced obvious cost per methane production, higher efficiency and less environmental issues.

In the latter case, where higher nitrogen content are utilised, the model did not produce any methane. These results are consistent with observations arising from previous methane production studies, results of which are summarised in FIGS. 4 & 5.

As further indicated in FIG. 4, that the effective concentration of nitrogen required to stimulate methane production has a biomodal peak and that while increasing nitrogen concentrations generally promote greater microbial activity in regard to methane production, an enhanced methane production peak is obtainable at unexpectedly low nitrogen to phosphorus ratios.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

Further, with regard to the various means referred to throughout the specification, any means is to be understood as encompassing individual as well as plural structures that may or may not be physically connected.

Clauses

1. A process of stimulating and maintaining the activity of a microbial consortia within a subterranean carbonaceous medium to produce methane comprising the steps of:
    a. dosing a first nutrient composition into the microbial consortia environment,
    b. monitoring the microbial consortia environment, including the generation of methane therein;
    c. dosing a second nutrient composition into the microbial consortia based upon the results of step (B); and
    d. repeating steps (B) and (C) and, if required,
    e. dosing a further nutrient composition into the microbial consortia environment based upon the results of step (D).

2. The process according to clause 1, wherein step (B) measures a peak methane generation rate and the second nutrient composition is dosed after the methane generation has dropped to less than 70% of the peak methane generation rate.

3. The process according to clause 2, wherein the second nutrient composition is dosed after the methane generation had dropped to less than 50% of the peak methane generation rate.

4. The process according to any one of the preceding clauses, wherein the second nutrient composition is dosed after the methane generation had dropped to no less than 1% of a peak methane generation rate.

5. The process according to any one of the preceding clauses, wherein the second nutrient composition is dosed after the methane generation had dropped no less than 10% of a peak methane generation rate.

6. The process according to any one of the preceding clauses, wherein the elapsed time between the end of dosing of the first nutrient composition and the start of dosing the second nutrient composition is between 30 days and 24 months.

7. The process according to clause 4, wherein the elapsed time between the end of dosing of the first nutrient composition and the start of dosing the second nutrient composition is between 2 months and 18 months.

8. The process according to clause 4, wherein the elapsed time between the end of dosing of the first nutrient composition and the start of dosing the second nutrient composition is between 4 months and 14 months.

9. The process according to any one of the preceding clauses, wherein the first nutrient composition and second or subsequent nutrient composition are different.

10. The process according to clauses 9 or 10, wherein the nitrogen concentration in the second composition is lower than the nitrogen concentration in the first nutrient composition.

11. The process according to any one of the preceding clauses, wherein the difference between the first nutrient composition and the second or subsequent nutrient composition is a relative decrease in the proportion of nitrogen relative to the total amount of nitrogen and phosphorus in the nutrient compositions.

12. The process according to any one of the preceding clauses, wherein the difference between the first nutrient composition and the second or subsequent nutrient composition is a relative decrease in the proportion of phosphorus relative to the total amount of nitrogen and phosphorus in the nutrient compositions.

13. The process according to any one of clauses 9 to 12, wherein the second nutrient composition comprises substantially no nitrogen.

14. The process according to any one of clauses 9 to 13, wherein the difference between the first nutrient composition and second or subsequent nutrient composition is determined by reference to one of more of differences in:
    a formation water;
    the carbonaceous medium; and
    the microbial consortia,
    between the dosing of the first nutrient composition and second or subsequent composition.

15. The process according to any one of the preceding clauses, wherein the first, second or further nutrient composition is determined through the use of an algorithm.

16. The process according to clause 15, wherein the algorithm is an adaptive learning algorithm.

17. The process according to clauses 15 or 16, wherein the algorithm calculates the proportion of nutrients available to the microbial consortia in the indigenous environment.
18. The process according to any one of clauses 15 to 17, wherein the algorithm draws upon comparative data from a different time, microbial consortia and/or carbonaceous material in determination of the first, second or further nutrient composition.
19. The process according to any one of clauses 15 to 18, wherein carbonaceous material is coal or carbonaceous shale and the algorithm uses the organic composition to determine the first, second or further nutrient composition.
20. The process according to any one of the preceding clauses, wherein the produced methane in recovered after an incubation period starting after the completion of the dosing of the first, second and/or further nutrient composition.
21. The process according to clause 20, wherein the incubation period is between one month and three years.
22. The process according to clauses 20 or 21, wherein the recovery of methane occurs as part of a cyclic process comprising a dosing phase, an incubation phase and a methane recovery phase.
23. The process according to clause 22, wherein the recovery of methane occurs over at least two process cycles.
24. The process according to any one of the preceding clauses wherein the dosing nutrient composition and amount of a second or further nutrient composition into the microbial consortia is based upon factors other than the generation of methane.
25. The process according to clause 24, wherein the dosing composition and amount of a second or further nutrient composition into the microbial consortia is based upon a monitoring of the formation water; the carbonaceous medium; and/or the microbial consortia.
26. The process according to any one of the preceding clauses, wherein the dosing composition and amount of a second or further nutrient composition is determined to compensate for changes in the microbial consortia environment since the dosing of the first nutrient composition.

| | | | | | | | | | | | | |
|---|---|---|---|---|---|---|---|---|---|---|---|---|
| Simulation experiments-Consortia 1 | | | | | | | | | | | | |
| Days (since start) Initial dose | Days (since last gas release) | P Dose (mg/L) | N Dose (mg/L) | Vol. mls | Gas Rate mls/1 day | $CH_4$ (%) | $CO_2$ (%) | $N_2$ (%) | Ar (%) | $H_2$ (%) | $CH_3$ rate/unit mg N | Change direction (change to baseline) |
| 1st dose | 0 | 400 | 100 | | | 0* | 0 | 0 | 95 | 5 | 0 | |
| 16 | 16 | — | — | 23.6 | 1.5(1.475) | 5.5186 | 4.2171 | 3.6967 | 72.609 | 0.0024 | 0.000814 | max ave rate (baseline) |
| 24 | 9 | — | — | 8.8 | 1.0(0.977) | 5.2731 | 3.7434 | 8.7251 | 66.6034 | 0.4368 | 0.000515 | Going ↓ to an unsampled minimum |
| $2^{nd}$ dose | 0 | 400 | 50 | | | | | | | | | |
| 12 | — | — | — | 4.75 | 0.4(0.396) | 5.8591 | 3.3867 | 6.4371 | 70.6035 | 0.3634 | 0.000455 | Going ↑ |
| 15 | — | — | — | 4.86 | 0.3(0.324) | 7.933** | 3.7296 | 5.1371 | 70.376 | 0.2112 | 0.000514* | Going ↑ |
| 1st dose | 0 | 400 | 100 | | | 0* | 0 | 0 | 95 | 5 | 0 | |
| | 14 | — | — | 0 | 0 | 0 | | | | | | |

*that peak observed methane generation rate here is substantially the same as the last sample of the first cycle incubation period—therefore, the system is performing as well writh 1/N for second cycle compared to N for first cycle.
**while the total gas volume recovered in the second cycle is less than the first cycle, the methane conversion activity is enhanced by the second 1/N dose compared to the first cycle, indicating an increased system efficiency for the second cycle using less N than the first dose

| | | | | | | | | |
|---|---|---|---|---|---|---|---|---|
| Theoretical-Over 2 cycles | | | | | | | | |
| Days (since start) Initial dose | Days (since last gas release) | P Dose (mg/L) | N Dose (mg/L) | Vol. mls | Gas Rate mls/1 day | $CH_4$ (%) | $CH_3$ rate/unit mg N | Change direction (change to baseline) |
| $1^{st}$ dose | 0 | 400 | 100 | | | | | |
| 16 | 16 | — | — | 23.6 | 1.5(1.475) | 5.5186 | 0.00081399 | max ave rate (baseline) |
| 24 | 9 | — | — | 8.8 | 1.0(0.977) | 5.2731 | 0.00051516 | Going ↓ |
| 24 | 0 | — | 100 | 0 | 0 | 0 | 0 | |
| $2^{nd}$ dose | 0 | 400 | | | | | | |
| 14 | 14 | — | — | 0 | 0 | 0 | 0 | ↓ |
| 29 | 15 | — | — | 4 | 0.267 | 1.5865 | 0.00423 mls methane/day Without extraneous N | Going ↑ |
| 43 | 14 | — | — | 6.7 | 0.0479 | 3.7577 | 0.017951692 mls methane/day without extraneous N | max ave rate-cycle 2 (X%↑) |

Notes:
↑ Indicates that the methane production is increasing, while ↓ indicates that the methane production isdecreasing after the maximum methane production inflection point has been achieved. It can be seen that over time a successive increase in the methane/unit N content occurs corresponding to increased methane production despite less nitrogen being provided for each dosing cycle.
the symbol "—" signifies no further additions to solution;
Coal feedstock = T79A;
Inocula = Talinga 58 feedwater;
RTP = (21° C., 1 atm pressure) (cm$^3$);
Gas Rate = (cm$^3$/day since last gas release);
Vol. = volume of gas evolved at RTP;
N Dose = (NH$_4$Cl mg/L);
P Dose = (K$_2$HPO$_4$ • 2H$_2$O mg/L);
Reductants = Na$_2$S • 9H$_2$O (250 mg/L)
Starting composition of anaerobic chamber atmosphere at time of bottling was 95% Ar, 5% H$_2$
Micro GC results, not normalised, 10% BOC Std analysed to bracket sample

| Theoretical examples-5 cycles | | | | | | | | |
|---|---|---|---|---|---|---|---|---|
| Days (since start) initial dose | Days (since last gas release) | P Dose (mg/L) | N Dose (mg/L) | Vol. mls | Gas Rate mls/1 day | CH$_4$ (%) | CH$_3$ rate/unit mg N | Change direction (change to baseline) |
| 1$^{st}$ dose | 0 | 400 | 100 | | | | | |
| 16 | 16 | — | — | 23.6 | 1.475 | 5.5186 | 0.00081399 | max ave rate (baseline) |
| 24 | 9 | — | — | 8.8 | 0.977 | 5.2731 | 0.00051518 | Going ↓ |
| 36 | 12 | — | — | 7.2 | 0.05 | 5.8591 | 0.000351546 | Going ↓ |
| 51 | 15 | — | — | 6.9 | 6.9 | 5.999 | 0.000275954 | Going ↓ |
| 2$^{nd}$ dose | 0 | 400 | 75 | | | | | |
| 52 | 14 | — | — | 19.5 | 1.393 | 5.2900 | 0.0009825 | Going ↑ |
| 62 | 10 | — | — | 15.0 | 1.50 | 5.405 | 0.0010710 | max ave rate-cycle 2 (↑ on baseline) |
| 70 | 8 | — | — | 8.5 | 1.06 | 5.153 | 0.0007300 | Going ↓ |
| 81 | 11 | — | — | 4.8 | 0.44 | 4.5988 | 0.0026756 | Going ↓ |
| 3$^{rd}$ dose | 0 | 400 | 50 | | | | | |
| 88 | 7 | — | — | 11.9 | 1.70 | 4.8015 | 0.0163251 | Going ↑ |
| 96 | 10 | — | — | 17 | 1.70 | 5.3555 | 0.0018207 | Going ↑ |
| 106 | 8 | — | — | 17.8 | 2.225 | 4.9111 | 0.0021854 | max ave rate-cycle 3 (↑ on baseline) |
| 118 | 12 | — | — | 21.5 | 1.79 | 4.8544 | 0.0017394 | Going ↓ |
| 4$^{th}$ dose | 0 | 400 | 25 | | | | | |
| 129 | 11 | — | — | 14.4 | 1.31 | 4.4451 | 0.0023276 | Going ↑ |
| 142 | 13 | — | — | 19.3 | 1.48 | 4.9512 | 0.0029400 | max ave rate-cycle 4 (↑ on baseline) |
| 150 | 8 | — | — | 9.5 | 1.19 | 4.3147 | 0.0020494 | Coing ↓ |
| 5$^{th}$ dose | 0 | 400 | 0 | | | | | |
| 160 | 10 | — | — | 0 | 0 | 0 | na | not productive |
| 180 | 20 | — | 0 | 4 | 0.2 | 0.025 | 0.00005 mls methane/day Without N | Going ↑ |

Notes:
↑ indicates that the methane production is increasing, while ↓ indicates that the methane production is decreasing after the maximum methane production inflection point has been achieved. It can be seen that over time a successive increase in the methane/unit N content occurs corresponding to increased methane production despite less nitrogen being provided for each dosing cycle.
Under dose heading the symbol "—" signifies no further additions to solution.
Coal feedstock = T79A;
Inocula = T58 feedwater;
RTP = (21° C., 1 atm pressure) (cm$^3$);
Gas Rate = (cm$^3$/day since last gas release);
Vol. = volume of gas evolved at RTP;
N Dose = (NH$_4$Cl mg/L);
P Dose = (K$_2$HPO$_4$ • 2H$_2$O mg/L);
Reductants = Na$_2$S • 9H$_2$O (250 mg/L)
Starting composition of anaerobic chamber atmosphere at time of bottling was 95% Ar, 5% H$_2$
Micro GC results, not normalised, 10% BOC Std analysed to bracket sample

40

| Theoretical-3 cycles | | | | | | |
|---|---|---|---|---|---|---|
| Days (since start) initial dose | Days (since last gas release) | P Dose (mg/L) | N Dose (mg/L) | CH$_4$ (%) | ave. daily contribution to methane (adc) %/day | adc normalised to N unit increasing with CH$_3$ conversion efficiency |
| 0 | 0 | 400 | 100 | 0 | 0 | |
| 16 | 16 | — | — | 5.5186 | 0.345 | 0.00345 |
| 24 | 9 | — | — | 5.2731 | 0.586 | 0.00588 |
| 36 | 12 | — | — | 5.111 | 0.426 | 0.00426 |
| 51 | 15 | — | — | 4.254 | 0.284 | 0.00284 |
| 2$^{nd}$ dose | 0 | 400 | 75 | | | |
| 52 | 14 | — | — | 5.29 | 0.378 | 0.00504 |
| 62 | 10 | — | — | 5.405 | 0.541 | 0.00721 |
| 70 | 8 | — | — | 5.153 | 0.644 | 0.00859 |
| 81 | 11 | — | — | 4.5088 | 0.418 | 0.00557 |
| 3$^{rd}$ dose | 0 | 400 | 50 | | | |
| 88 | 7 | — | — | 4.8015 | 0.688 | 0.01372 |
| 96 | 10 | — | — | 5.3555 | 0.536 | 0.01071 |
| 106 | 8 | — | — | 4.9111 | 0.614 | 0.01228 |
| 118 | 12 | — | — | 4.8544 | 0.405 | 0.00809 |

| Days (since start) initial dose | Days (since last gas release) | P Dose (mg/L) | N Dose (mg/L) | Vol. mls | Gas Rate mls/1 day | CH$_4$ (%) |
|---|---|---|---|---|---|---|
| 1st dose | 0 | 400 | 100 | | | |
| 16 | 16 | — | — | 23.6 | 1.5(1.475) | 5.5186 |
| 24 | 9 | — | — | 8.8 | 1.0(0.977) | 5.2731 |
| 2$^{nd}$ dose | 0 | 400 | 50 | | | |
| | 12 | — | — | 4.76 | 0.4(0.396) | 5.8591 |
| | 15 | — | — | 4.86 | 0.3(0.324) | 7.933 |

| Days (since start) initial dose | Days (since last gas release) | P Dose (mg/L) | N Dose (mg/L) | CH$_4$ (%) | CO$_2$ (%) | N$_2$ (%) | Ar (%) | H$_2$ (%) | ave. daily contribution to methane (adc) %/day | adc normalised to N unit increasing with CH3 conversion efficiency |
|---|---|---|---|---|---|---|---|---|---|---|
| 0 | 0 | 400 | 100 | 0 | 0 | 0 | 95 | 5 | 0 | |
| 16 | 16 | — | — | 5.5186 | 4.2171 | 3.6967 | 72.609 | 0.0024 | 0.34491 | 0.003449 |
| 24 | 9 | — | — | 5.2731 | 3.7434 | 8.7251 | 68.6034 | 0.4368 | 0.58590 | 0.005859 |
| 0 | 0 | 400 | 100 | | | | | | | |
| 36 | 12 | — | — | 5.8591 | 3.3867 | 6.4371 | 70.5036 | 0.3634 | 0.48626 | 0.009765↑ |
| 51 | 15 | — | — | 7.933 | 3.7295 | 5.1371 | 70.378 | 0.2112 | 0.52877 | 0.010577↑ |

The invention claimed is:

1. A process of stimulating and maintaining an activity of a microbial consortia within a subterranean solid carbonaceous medium to produce methane, the process comprising the steps of:
   A. dosing a first nutrient composition into the subterranean solid carbonaceous medium;
   B. monitoring generation of methane in the subterranean solid carbonaceous medium;
   C. dosing a second nutrient composition into the subterranean solid carbonaceous medium based upon the results of step (B); and
   D. repeating steps (B) and (C) and, if required,
   E. dosing a further nutrient composition into the subterranean solid carbonaceous medium based upon the results of step (D),
   wherein step (B) measures a parameter associated with generation of methane, wherein the second nutrient composition is closed after the generation of methane has dropped to less than 90% of a peak methane generation parameter, and wherein the peak methane generation parameter monitored over a given monitoring/incubation period (B) is one or more of:
      i. a peak rate of methane production per unit nitrogen $(M_r/N)^n$ resulting from a nitrogen concentration added in the second $(Nc)^2$ or subsequent $(Nc)^n$ nutrient composition dosages is higher than a peak rate of methane production per unit nitrogen $(M_r/N)^1$ observed for the initial nutritional composition dosage $(Nc)^1$, wherein n is an integer equal to a dose of 2 or greater;
      ii. a peak rate of methane production per unit nitrogen $(M_r/N)^n$ resulting from the nitrogen concentration added in a second $(Nc)^2$ or subsequent $(Nc)^n$ nutrient composition dosages is higher than a peak rate of methane production per unit nitrogen $(M_r/N)$ observed for an initial nutritional composition dosage, than had the second or subsequent dosages the same or higher nitrogen concentration $(Nc)^n$ than the initial nitrogen dosage concentration $(Nc)^1$, wherein n is an integer equal to a dose of 2 or greater;
      iii. a peak average daily % contribution to a sample methane composition over a sampling period $(ave)^1 >$ $(ave)^n$, 1 wherein n is an integer equal to a dose of 2 or greater;
      iv. peak mole of methane generated per volume of methane gas, where (moles/unit volume methane gas)> (moles/unit volume methane gas)$^n$, 1 wherein n is an integer equal to a dose of 2 or greater; and
      v. average amount of methane generated during the period.

2. The process according to claim 1, wherein the second nutrient composition is dosed after the methane generation has dropped to less than 70% of a peak methane generation parameter.

3. The process according to claim 1, wherein the second nutrient composition is dosed after the methane generation had dropped to no less than 1% of a peak methane generation parameter.

4. The process according to claim 1 wherein the parameter associated with methane generation is one or more of:
   (i) methane generation;
   (ii) average daily rate of methane generation over a monitoring/incubation period (B);
   (ii) average daily % contribution to a sample methane composition over a monitoring/incubation period (B);
   (iii) average amount of methane generated over a monitoring/incubation period (B); and
   (iv) gas pressure, partial pressure, a thermal or ionic conductivity or isotopic ratio measurements associated with methane gas composition concentration.

5. The process according to claim 4, wherein the methane generation is measured as % methane/volume, moles or mole % of methane/volume.

6. The process according to claim 1, wherein the elapsed time between the end of dosing of the first nutrient composition and the start of dosing the second nutrient composition is between 7 days and 30 months.

7. The process according to claim 1, wherein the first nutrient composition and second or subsequent nutrient composition are different.

8. The process according to claim 1, wherein a nitrogen concentration in the second nutrient composition is lower than a nitrogen concentration in the first nutrient composition.

9. The process according to claim 1, wherein the difference between the first nutrient composition and the second or subsequent nutrient composition is a relative decrease in the proportion of nitrogen relative to the total amount of nitrogen and phosphorus in the nutrient compositions.

10. The process according to claim 9, wherein the decrease is 75%, 50% or 25% of the amount of nitrogen in the first nutrient composition.

11. The process according to claim 1, wherein the difference between the first nutrient composition and the second or subsequent nutrient composition is a relative decrease in the proportion of phosphorus relative to the total amount of nitrogen and phosphorus in the nutrient compositions.

12. The process according to claim 1, wherein the second nutrient composition comprises substantially no nitrogen.

13. The process according to claim 1, wherein the difference between the first nutrient composition and second or subsequent nutrient composition is determined by reference to one of more of differences in:
   a formation water;
   the carbonaceous medium; and
   the microbial consortia,
between the dosing of the first nutrient composition and second or subsequent composition.

14. The process according to claim 1, wherein the first, second or further nutrient composition is determined through the use of an algorithm.

15. The process according to claim 14, wherein the algorithm calculates the proportion of nutrients available to the microbial consortia in an associated indigenous environment.

16. The process according to claim 14, wherein the algorithm draws upon comparative data from a different time, the microbial consortia and/or the subterranean solid carbonaceous medium in determination of the first, second or further nutrient composition.

17. The process according to claim 14, wherein the subterranean solid carbonaceous medium is coal or carbonaceous shale and the algorithm uses the organic composition to determine the first, second or further nutrient composition.

18. The process according to claim 14, wherein the produced methane is recovered after an incubation period starting after the completion of the dosing of the first, second and/or further nutrient composition.

19. The process according to claim 18, wherein the incubation period is between 7 days and three years.

20. The process according to claim 18, wherein the recovery of methane occurs as part of a cyclic process comprising a dosing phase, an incubation phase and a methane recovery phase.

21. The process according to claim 20, wherein the recovery occurs over at least two process cycles.

22. The process according to claim 1, wherein the dosing nutrient composition and amount of a second or further nutrient composition into the microbial consortia is based upon factors other than the generation of methane; a formation water; the carbonaceous medium; and/or the microbial consortia and/or wherein the dosing composition and amount of a second or further nutrient composition is determined to compensate for changes in the microbial consortia environment since the dosing of the first nutrient composition.

* * * * *